(12) United States Patent
Adams et al.

(10) Patent No.: US 7,932,088 B1
(45) Date of Patent: Apr. 26, 2011

(54) HIGH EFFICIENCY TRANSFORMATION OF PLASMODIUM FALCIPARUM BY THE LEPIDOPTERAN TRANSPOSON, PIGGYBAC

(75) Inventors: John H. Adams, Granger, IN (US); Malcolm J. Fraser, Granger, IN (US); Bharath Balu, South Bend, IN (US); Douglas A. Shoue, North Liberty, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 481 days.

(21) Appl. No.: 11/410,333

(22) Filed: Apr. 25, 2006

Related U.S. Application Data

(60) Provisional application No. 60/674,312, filed on Apr. 25, 2005.

(51) Int. Cl.
*C12N 15/74* (2006.01)
*C12N 15/82* (2006.01)
*C12N 15/87* (2006.01)
*A01H 1/00* (2006.01)

(52) U.S. Cl. .................. 435/473; 800/291
(58) Field of Classification Search .............. 435/473; 800/291
See application file for complete search history.

(56) References Cited

U.S. PATENT DOCUMENTS 7,129,083 B1 * 10/2006 Handler ............... 435/320.1

OTHER PUBLICATIONS

Balu, B. Apr. 7, 2005 "Genetic Analysis of *Plasmodium falciparum*" Dissertation pp. 1-117.*
Gardiner et al 2003 Trends in Parasitology vol. 19 Issue 9 pp. 381-383.*
Nolan et al 2002 The Journal of Biological Chemistry vol. 277 No. 11 pp. 8759-8762.*
Mamoun et al 2000 Molecular and Biochemical Parasitology vol. 110 pp. 405-407.*
Bowie et al Science, 1990, 247:1306-1310.*
Trang et al Malaria Journal 2004 vol. 3 No. 7 pp. 1-7.*
Cummins et al Mar. 15, 2001 ISIS Report pp. 1-3.*
Wu et al 1996 Proc. Natl. Acad. Sci. vol. 93 pp. 1130-1134.*
Wu et al 1995 Proc. Natl. Acad. Sci. vol. 92 pp. 973-977.*
Cary et al 1989 Virology vol. 172 pp. 156-169.*
Dijk, et al., "Stable Transfection of Malaria Parasite Blood Stages," Science, 1995, pp. 1358-1362, v. 268.
Crabb, et al., "Characterization of promoters and stable transfection by homologous and nonhomologous recombination in *Plasmodium falciparum*," Proc. Natl. Acad. Sci. USA, 1996, pp. 7289-7294, v. 93, Medical Sciences.
Waters, et al., "Transfection of Malaria Parasites," Methods: A Companion to Methods in Enzymology, 1997, pp. 134-147, v. 13, Academic Press.
Wu, et al., "Transformation of *Plasmodium falciparum* malaria parasites by homologous integration of plasmids that confer resistance to pyrimethamine," Proc. Natl. Acad. Sci. USA, 1996, pp. 1130-1134, v. 93, Genetics.
Greenwood, et al., "Malaria in 2002," Nature, 2002, pp. 670-672, v. 415, Macmillan Magazines Ltd.
Maitland, et al. "Falciparum malaria: current therapeutic challenges," Current Opinion in Infectious Diseases, 2004, pp. 405-412, v. 17, Lippincott Wiliams & Wilkins.
Winstanley, et al. "Therapy of Falciparum Malaria in Sub-Saharan Africa: from Molecule to Policy," Clinical Microbiology Reviews, 2004, pp. 612-637, v. 17 No. 3, American Society for Microbiology.
Breman, et al. "Conquering the Intolerable Burden of Malaria: What's New, What's Needed: A Summary," Am. J. Trop. Med. Hyg., 2004, pp. 1-15, The American Society of Tropical Medicine and Hygiene.
Hartl, Daniel L., "The Origin of Malaria: Mixed Messages from Genetic Diversity," Nature Reviews, 2004, pp. 15-22, v. 2.
Gueiros-Filho, et al., "Trans-kingdom Transposition of the Drosophila Element mariner Within the Protozoan Leishmania," Science, 1997, pp. 1716-1719, v. 276.
Fraser, et al., "Acquisition of Host Cell DNA Sequences by Baculoviruses: Relationship Between Host DNA Insertions and FP Mutants of *Autographa californica* and *Galleria mellonella* Nuclear Polyhedrosis Viruses," Journal of Virology, 1983, pp. 287-300, v. 47 No. 2, American Society for Microbiology.
Fraser, et al., "Transposon-Mediated Mutagenesis of a Baculovirus," Virology, 1985, pp. 356-361, v. 145, Academic Press, Inc.
Cary, et al., "Transposon Mutagenesis of Baculoviruses: Analysis of Trichplusia ni Transposon IFP2 Insertions within the FP-Locus of Nuclear Polyhedrosis Viruses," Virology, 1989, pp. 156-169, v. 172, Academic Press, Inc.
Thibault, et al., "A complementary transposon tool kit for *Drosophila melanogaster* using P and *piggyBac*," Nature Genetics, 2004, pp. 283-287, v. 36 No. 3.
Lobo, et al., "Germ line transformation of the yellow fever mosquito, *Aedis aegypti*, mediated by transpositional insertion of a *piggyBac* vector," Insect Molecular Biology, 2002, pp. 133-139, v. 11(2), Royal Entomological Society.
Grossman, et al., "The *piggyBac* element is capable of precise excision and transposition in cells and embryos of the mosquito, *Anopheles gambiae*," Insect Biochemistry and Molecular Biology, 2000, pp. 909-914, v. 30, Elsevier Science Ltd.

(Continued)

*Primary Examiner* — Patricia A Duffy
*Assistant Examiner* — Nina A Archie
(74) *Attorney, Agent, or Firm* — Denise L. Mayfield; Katten Muchin Rosenman LLP

(57) ABSTRACT

The present invention provides molecular methods for efficiently transforming the genome of common disease-transmitting parasites, such as *Plasmodium falciparum*. The transformation efficiencies are improved up to 100 times over those conventionally known. The methods provide high saturation of the target parasite genome, of 50% or greater, and target non-specifically TTAA-rich sites in the parasite genome. The invention also discloses a model that may be used to functionally annotate the genome of the *Plasmodium falciparum*, thus permitting the design and screening of compounds that may be useful in the control and inhibiting of diseases caused and transmitted by these parasites, including malaria. Highly efficient and multi-site integrating transposons, particularly piggyBac transposons, which provide for random and multi-site integration into parasite genomes in the presence of a helper plasmid, are also presented.

29 Claims, 8 Drawing Sheets

OTHER PUBLICATIONS

Figure 1A:
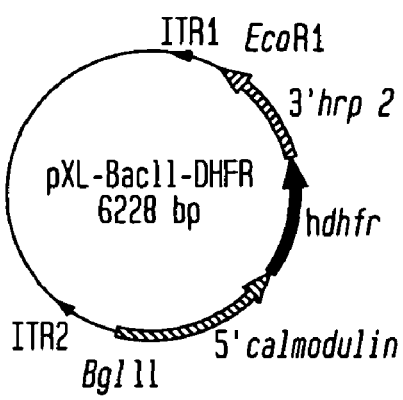

Li, et al., "*piggyBac* internal sequences are necessary for efficient transformation of target genomes," Insect Molecular Biology, 2005, pp. 17-30, v. 14(1), The Royal Entomological Society.

Deitsch, et al., "Transformation of malaria parasites by the spontaneous uptake and expression of DNA from human erythrocytes," Nucleic Acids Research, 2001, pp. 850-853, v. 29 No. 3.

Toshiki, et al., "Germline transformation of the silkworm *Bombyx mori* L. using a *piggyBac* transposon-derived vector," Nature Biotechnology, 2000, pp. 81-84, v. 18, Nature America Inc.

O'Donnel, et al., "A genetic screen for improved plasmid segregation reveals a role for Rep20 in the interaction of *Plasmodium falciparum* chromosomes," The EMBO Journal, 2002, pp. 1231-1239, v. 21 No. 5, European Molecular Biology Organization.

Sarkar et al., "Molecular evolutionary analysis of the widespread *piggyBac* transposon family and related "domesticated"sequences," Mol Gen Genomics, 2003, pp. 173-180, v. 270, Springer-Verlag.

Mamoun, et al., "Transposition of the *Drosophila* element mariner within the human malaria parasite *Plasmodium falciparum*," Molecular and Biochemical Parasitology, 200, pp. 405-407, v. 110, Elsevier Science B.V, (2000).

Ryder, et al., "Transposable elements as tools for genomics and genetics in *Drosophila*," Briefings in Functional Genomics and Protoeomics, 2003, pp. 57-71, v. 2 No. 1, & Henry Steward Publications.

Trang, et al., "One-step concentration of malarial parasite-infected red blood cells and removal of contaminating white blood cells," 2004, Malaria Journal, pp. 1-7, BioMed Central.

Earp, et al., "Amplification of genomic sequences flanking transposable elements in host and heterologous plants: a tool for transposon tagging and genome characterization," Nucleic Acids Research, 1990, pp. 3271-3279, v. 18 No. 11.

Gardner, et al., "Genome sequence of the human malaria parasite *Plasmodium falciparum*," Nature, 2002, pp. 498-511, v. 419, Nature Publishing Group.

Watanabe, et al., "Full-malaria: a database for full-length enriched cDNA library from human malaria parasite, *Plasmodium falciparum*," Nucleic Acids Research, 2001, pp. 70-71, v. 29 No. 1, Oxford University Press.

Kadekoppala, et al., "Rapid recominbation among transfected plasmids, chimeric episome formation and trans gene expression in *Plasmodium falciparum*," Molecular & Biochemical Parasitology, 2001, pp. 211-218, v. 112, Elsevier Science B.V.

Schlichtherle, et al., "Methods in Malaria Research," 2000, pp. li-77.

Wang, et al., "Transposon mutagenesis of baculoviruses: analysis of TFP3 lepidopteran transposon insertions at the FP locus of nuclear polyhedrosis viruses," Gene, 1989, pp. 97-108, Elsevier Science Publishers B.V.

\* cited by examiner

FIG. 4

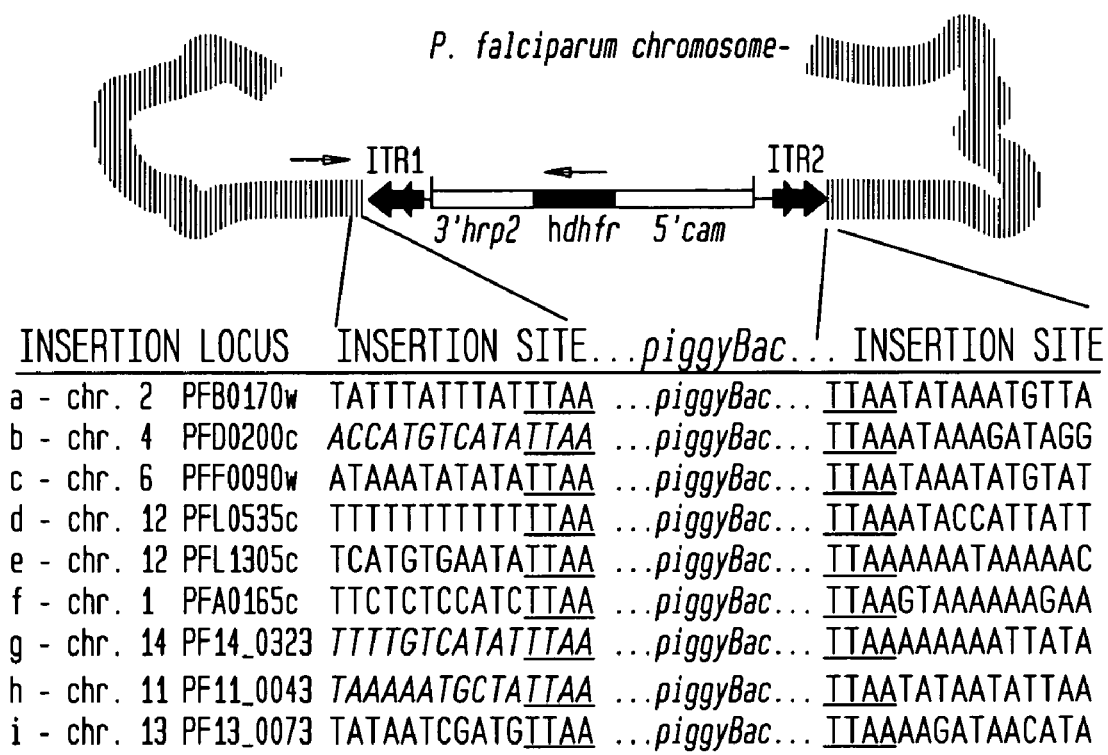

| INSERTION LOCUS | INSERTION SITE | ...piggyBac... | INSERTION SITE |
|---|---|---|---|
| a - chr. 2 PFB0170w | TATTTATTTAT*TTAA* | ...piggyBac... | *TTAA*TATAAATGTTA |
| b - chr. 4 PFD0200c | ACCATGTCATA*TTAA* | ...piggyBac... | *TTAA*ATAAAGATAGG |
| c - chr. 6 PFF0090w | ATAAATATATA*TTAA* | ...piggyBac... | *TTAA*TAAATATGTAT |
| d - chr. 12 PFL0535c | TTTTTTTTTT*TTAA* | ...piggyBac... | *TTAA*ATACCATTATT |
| e - chr. 12 PFL1305c | TCATGTGAATA*TTAA* | ...piggyBac... | *TTAA*AAAATAAAAAC |
| f - chr. 1 PFA0165c | TTCTCTCCATC*TTAA* | ...piggyBac... | *TTAA*GTAAAAAAGAA |
| g - chr. 14 PF14_0323 | TTTTGTCATAT*TTAA* | ...piggyBac... | *TTAA*AAAAAATTATA |
| h - chr. 11 PF11_0043 | TAAAAATGCTA*TTAA* | ...piggyBac... | *TTAA*TATAATATTAA |
| i - chr. 13 PF13_0073 | TATAATCGATG*TTAA* | ...piggyBac... | *TTAA*AAGATAACATA |

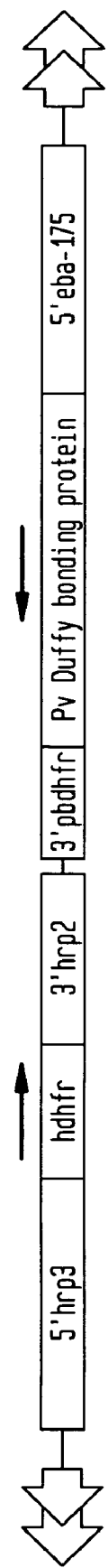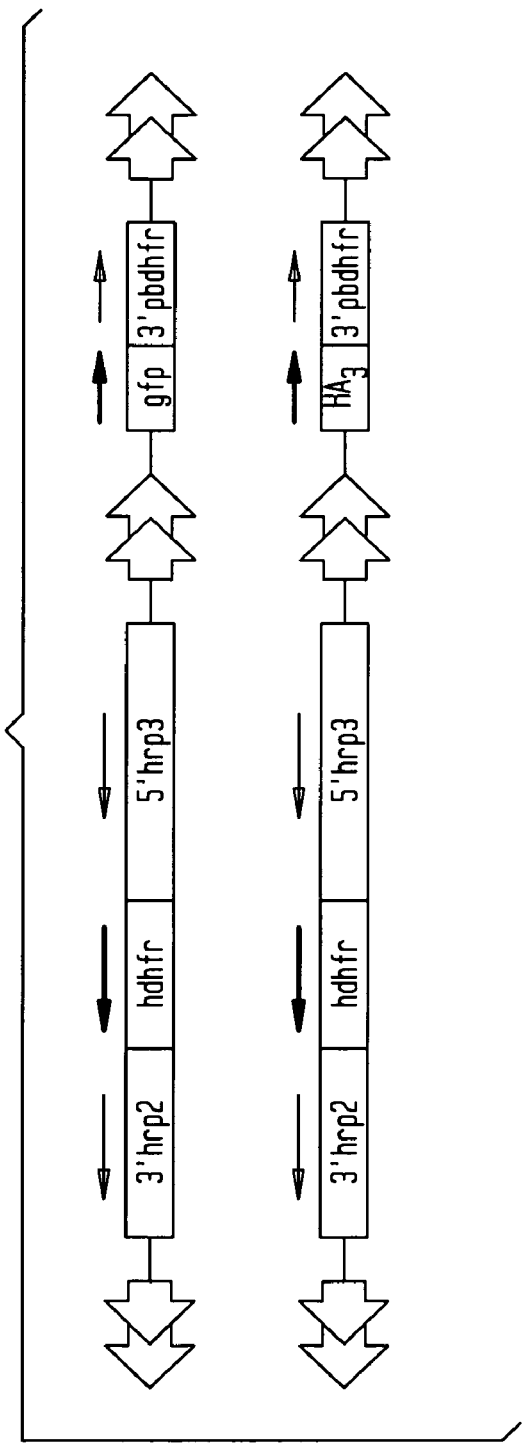
FIG. 11
FIG. 12

SEQUENCE LISTING

<160> NUMBER OF SEQ ID NOS: 20

<210> SEQ ID NO 1
<211> LENGTH: 1785
<212> TYPE: DNA
<213> ORGANISM: Artificial Sequence
<220> FEATURE:
<223> OTHER INFORMATION: Description of Artificial Sequence:
      Synthetic piggyBac construct
<220> FEATURE:
<221> NAME/KEY: CDS
<222> LOCATION: (1)..(1782)

<400> SEQUENCE: 1

| atg | ggt | agt | tct | tta | gac | gat | gag | cat | atc | ctc | tct | gct | ctt | ctg | caa | 48 |
| Met | Gly | Ser | Ser | Leu | Asp | Asp | Glu | His | Ile | Leu | Ser | Ala | Leu | Leu | Gln | |
| 1 | | | | 5 | | | | | 10 | | | | | 15 | | |

| agc | gat | gac | gag | ctt | gtt | ggt | gag | gat | tct | gac | agt | gaa | ata | tca | gat | 96 |
| Ser | Asp | Asp | Glu | Leu | Val | Gly | Glu | Asp | Ser | Asp | Ser | Glu | Ile | Ser | Asp |
| | | 20 | | | | | 25 | | | | | 30 | | | | |

| cac | gta | agt | gaa | gat | gac | gtc | cag | agc | gat | aca | gaa | gaa | gcg | ttt | ata | 144 |
| His | Val | Ser | Glu | Asp | Asp | Val | Gln | Ser | Asp | Thr | Glu | Glu | Ala | Phe | Ile |
| | | | 35 | | | | | 40 | | | | | 45 | | | |

| gat | gag | gta | cat | gaa | gtg | cag | cca | acg | tca | agc | ggt | agt | gaa | ata | tta | 192 |
| Asp | Glu | Val | His | Glu | Val | Gln | Pro | Thr | Ser | Ser | Gly | Ser | Glu | Ile | Leu |
| 50 | | | | | 55 | | | | | 60 | | | | | | |

| gac | gaa | caa | aat | gtt | att | gaa | caa | cca | ggt | tct | tca | ttg | gct | tct | aac | 240 |
| Asp | Glu | Gln | Asn | Val | Ile | Glu | Gln | Pro | Gly | Ser | Ser | Leu | Ala | Ser | Asn |
| 65 | | | | 70 | | | | | 75 | | | | | 80 | | |

| aga | atc | ttg | acc | ttg | cca | cag | agg | act | att | aga | ggt | aag | aat | aaa | cat | 288 |
| Arg | Ile | Leu | Thr | Leu | Pro | Gln | Arg | Thr | Ile | Arg | Gly | Lys | Asn | Lys | His |
| | | | | 85 | | | | | 90 | | | | | 95 | | |

| tgt | tgg | tca | act | tca | aag | tcc | acg | agg | cgt | agc | cga | gtc | tct | gca | ctg | 336 |
| Cys | Trp | Ser | Thr | Ser | Lys | Ser | Thr | Arg | Arg | Ser | Arg | Val | Ser | Ala | Leu |
| | | | 100 | | | | | 105 | | | | | 110 | | | |

| aac | att | gtc | aga | tct | caa | aga | ggt | ccg | acg | cgt | atg | tgc | cgc | aat | ata | 384 |
| Asn | Ile | Val | Arg | Ser | Gln | Arg | Gly | Pro | Thr | Arg | Met | Cys | Arg | Asn | Ile |
| | | | 115 | | | | | 120 | | | | | 125 | | | |

| tat | gac | cca | ctt | tta | tgc | ttc | aaa | cta | ttt | ttt | act | gat | gag | ata | att | 432 |
| Tyr | Asp | Pro | Leu | Leu | Cys | Phe | Lys | Leu | Phe | Phe | Thr | Asp | Glu | Ile | Ile |
| 130 | | | | | 135 | | | | | 140 | | | | | | |

| tcg | gaa | att | gta | aaa | tgg | aca | aat | gct | gag | ata | tca | ttg | aaa | cgt | cgg | 480 |
| Ser | Glu | Ile | Val | Lys | Trp | Thr | Asn | Ala | Glu | Ile | Ser | Leu | Lys | Arg | Arg |
| 145 | | | | 150 | | | | | 155 | | | | | 160 | | |

| gaa | tct | atg | aca | ggt | gct | aca | ttt | cgt | gac | acg | aat | gaa | gat | gaa | atc | 528 |
| Glu | Ser | Met | Thr | Gly | Ala | Thr | Phe | Arg | Asp | Thr | Asn | Glu | Asp | Glu | Ile |
| | | | 165 | | | | | 170 | | | | | 175 | | | |

| tat | gct | ttc | ttt | ggt | att | ctg | gta | atg | aca | gca | gtg | aga | aaa | gat | aay | 576 |
| Tyr | Ala | Phe | Phe | Gly | Ile | Leu | Val | Met | Thr | Ala | Val | Arg | Lys | Asp | Asn |
| | | | 180 | | | | | 185 | | | | | 190 | | | |

| cac | atg | tcc | aca | gat | gac | ctc | ttt | gat | cga | tct | ttg | tca | atg | gtg | tac | 624 |
| His | Met | Ser | Thr | Asp | Asp | Leu | Phe | Asp | Arg | Ser | Leu | Ser | Met | Val | Tyr |
| | | | 195 | | | | | 200 | | | | | 205 | | | |

| gtc | tct | gta | atg | agt | cgt | gat | cgt | ttt | gat | ttt | ttg | ata | cga | tgt | ctt | 672 |
| Val | Ser | Val | Met | Ser | Arg | Asp | Arg | Phe | Asp | Phe | Leu | Ile | Arg | Cys | Leu |
| | | 210 | | | | | 215 | | | | | 220 | | | | |

| aga | atg | gat | gac | aaa | agt | ata | cgg | ccc | aca | ctt | cga | gaa | aac | gat | gta | 720 |
| Arg | Met | Asp | Asp | Lys | Ser | Ile | Arg | Pro | Thr | Leu | Arg | Glu | Asn | Asp | Val |
| 225 | | | | 230 | | | | | 235 | | | | | 240 | | |

| ttt | act | cct | gtt | aga | aaa | ata | tgg | gat | ctc | ttt | atc | cat | cag | tgc | ata | 768 |
| Phe | Thr | Pro | Val | Arg | Lys | Ile | Trp | Asp | Leu | Phe | Ile | His | Gln | Cys | Ile |

```
                    245                 250                 255
caa aat tac act cca ggg gct cat ttg acc ata gat gaa cag tta ctt      816
Gln Asn Tyr Thr Pro Gly Ala His Leu Thr Ile Asp Glu Gln Leu Leu
        260                 265                 270 ggt ttt aga gga cgg tgt ccg ttt agg atg tat atc cca aac aag cca      864
Gly Phe Arg Gly Arg Cys Pro Phe Arg Met Tyr Ile Pro Asn Lys Pro
            275                 280                 285 agt aag tat gga ata aaa atc ctc atg atg tgt gac agt ggt acg aag      912
Ser Lys Tyr Gly Ile Lys Ile Leu Met Met Cys Asp Ser Gly Thr Lys
        290                 295                 300 tat atg ata aat gga atg cct tat ttg gga aga gga aca cag acc aac      960
Tyr Met Ile Asn Gly Met Pro Tyr Leu Gly Arg Gly Thr Gln Thr Asn
305                 310                 315                 320 gga gta cca ctc ggt gaa tac tac gtg aag gag tta tca aag cct gtg     1008
Gly Val Pro Leu Gly Glu Tyr Tyr Val Lys Glu Leu Ser Lys Pro Val
                325                 330                 335 cac ggt agt tgt cgt aat att acg tgt gac aat tgg ttc acc tca atc     1056
His Gly Ser Cys Arg Asn Ile Thr Cys Asp Asn Trp Phe Thr Ser Ile
            340                 345                 350 cct ttg gca aaa aac tta cta caa gaa ccg tat aag tta acc att gtg     1104
Pro Leu Ala Lys Asn Leu Leu Gln Glu Pro Tyr Lys Leu Thr Ile Val
        355                 360                 365 gga acc gtg cga tca aac aaa cgc gag ata ccg gaa gta ctg aaa aac     1152
Gly Thr Val Arg Ser Asn Lys Arg Glu Ile Pro Glu Val Leu Lys Asn
    370                 375                 380 agt cgc tcc agg cca gtg gga aca tcg atg ttt tgt ttt gac gga ccc     1200
Ser Arg Ser Arg Pro Val Gly Thr Ser Met Phe Cys Phe Asp Gly Pro
385                 390                 395                 400 ctt act ctc gtc tca tat aaa ccg aag cca gct aag atg gta tac tta     1248
Leu Thr Leu Val Ser Tyr Lys Pro Lys Pro Ala Lys Met Val Tyr Leu
                405                 410                 415 tta tca tct tgt gat gag gat gct tct atc aac gaa agt acc ggt aaa     1296
Leu Ser Ser Cys Asp Glu Asp Ala Ser Ile Asn Glu Ser Thr Gly Lys
            420                 425                 430 ccg caa atg gtt atg tat tat aat caa act aaa ggc gga gtg gac acg     1344
Pro Gln Met Val Met Tyr Tyr Asn Gln Thr Lys Gly Gly Val Asp Thr
        435                 440                 445 cta gac caa atg tgt tct gtg atg acc tgc agt agg aag acg aat agg     1392
Leu Asp Gln Met Cys Ser Val Met Thr Cys Ser Arg Lys Thr Asn Arg
    450                 455                 460 tgg cct atg gca tta ttg tac gga atg ata aac att gcc tgc ata aat     1440
Trp Pro Met Ala Leu Leu Tyr Gly Met Ile Asn Ile Ala Cys Ile Asn
465                 470                 475                 480 tct ttt att ata tac agc cat aat gtc agt agc aag gga gaa aag gtc     1488
Ser Phe Ile Ile Tyr Ser His Asn Val Ser Ser Lys Gly Glu Lys Val
                485                 490                 495 caa agt cgc aaa aaa ttt atg aga aac ctt tac atg agc ctg acg tca     1536
Gln Ser Arg Lys Lys Phe Met Arg Asn Leu Tyr Met Ser Leu Thr Ser
            500                 505                 510 tcg ttt atg cgt aag cgt tta gaa gct cct act ttg aag aga tat ttg     1584
Ser Phe Met Arg Lys Arg Leu Glu Ala Pro Thr Leu Lys Arg Tyr Leu
        515                 520                 525 cgc gat aat atc tct aat att ttg cca aat gaa gtg cct ggt aca tca     1632
Arg Asp Asn Ile Ser Asn Ile Leu Pro Asn Glu Val Pro Gly Thr Ser
    530                 535                 540 gat gac agt act gaa gag cca gta atg aaa aaa cgt act tac tgt act     1680
Asp Asp Ser Thr Glu Glu Pro Val Met Lys Lys Arg Thr Tyr Cys Thr
545                 550                 555                 560 tac tgc ccc tct aaa ata agg cga aag gca aat gca tcg tgc aaa aaa     1728
Tyr Cys Pro Ser Lys Ile Arg Arg Lys Ala Asn Ala Ser Cys Lys Lys
```

```
                565                 570                 575
tgc aaa aaa gtt att tgt cga gag cat aat att gat atg tgc caa agt     1776
Cys Lys Lys Val Ile Cys Arg Glu His Asn Ile Asp Met Cys Gln Ser
        580                 585                 590 tgt ttc tga                                                         1785
Cys Phe
```

<210> SEQ ID NO 2
<211> LENGTH: 594
<212> TYPE: PRT
<213> ORGANISM: Artificial Sequence
<220> FEATURE:
<223> OTHER INFORMATION: Description of Artificial Sequence:
      Synthetic piggyBac construct

<400> SEQUENCE: 2

```
Met Gly Ser Ser Leu Asp Asp Glu His Ile Leu Ser Ala Leu Leu Gln
 1               5                  10                  15

Ser Asp Asp Glu Leu Val Gly Glu Asp Ser Asp Ser Glu Ile Ser Asp
             20                  25                  30

His Val Ser Glu Asp Asp Val Gln Ser Asp Thr Glu Glu Ala Phe Ile
         35                  40                  45

Asp Glu Val His Glu Val Gln Pro Thr Ser Gly Ser Glu Ile Leu
     50                  55                  60

Asp Glu Gln Asn Val Ile Glu Gln Pro Gly Ser Ser Leu Ala Ser Asn
 65                  70                  75                  80

Arg Ile Leu Thr Leu Pro Gln Arg Thr Ile Arg Gly Lys Asn Lys His
                 85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320
```

```
Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 3
tatttattta tttaa                                                    15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 4
ttaatataaa tgtta                                                    15
```

```
<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 5
accatgtcat attaa                                                          15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 6
ttaaataaag atagg                                                          15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 7
ataaatatat attaa                                                          15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 8
ttaataaata tgtat                                                          15

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 9
tttttttttt tttaa                                                          15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 10
ttaaatacca ttatt                                                          15

<210> SEQ ID NO 11
<211> LENGTH: 15
```

```
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 11
tcatgtgaat attaa                                                    15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 12
ttaaaaaata aaaac                                                    15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 13
ttctctccat cttaa                                                    15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 14
ttaagtaaaa aagaa                                                    15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 15
ttttgtcata tttaa                                                    15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 16
ttaaaaaaaa ttata                                                    15

<210> SEQ ID NO 17
<211> LENGTH: 15
<212> TYPE: DNA
<213> ORGANISM: Artificial Sequence
```

```
<220> FEATURE:
<223> OTHER INFORMATION: Description of Artificial Sequence:
      Synthetic oligonucleotide

<400> SEQUENCE: 17
taaaaatgct attaa                                                            15

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 18
ttaatataat attaa                                                            15

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 19
tataatcgat gttaa                                                            15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 20
ttaaaagata acata                                                            15
```

HIGH EFFICIENCY TRANSFORMATION OF PLASMODIUM FALCIPARUM BY THE LEPIDOPTERAN TRANSPOSON, PIGGYBAC

CROSS-REFERENCE TO RELATED APPLICATIONS

This application claims priority from U.S. Provisional Application No. 60/674,312, filed Apr. 25, 2005, entitled "Transposon-Mediated Mutagenesis Of Plasmodium Falciparum," which is hereby incorporated by reference herein in its entirety.

GOVERNMENT INTEREST STATEMENT

The United States Government has rights in this invention pursuant to National Institutes of Health (NIH) Grant No. RO1 AI33656 and RO1 AI48561.

BACKGROUND

1. Field of the Invention

The present invention relates generally to the genetic manipulation of a parasite genome (such as Plasmodium falciparum) through the use of a piggyBac transposable element construct, as well as to piggyBac transposable element constructs themselves, and for applications to identify, characterize, and/or create therapies protective in people against malaria. The field of the invention also relates to the field of malaria, and methods for controlling malarial-transmitting organisms such as Plasmodium falciparum through the use of the herein described piggyBac constructs.

2. Related Art

Malaria is a deadly infectious disease annually causing clinical illness in 400-600 million people, and killing millions.[5] Caused by several different Plasmodium species, malaria remains endemic in many tropical and temperate climates. Traditional measures to control malaria are becoming increasingly ineffective due to widespread resistance against many of the available antimalarial drugs and insecticide resistance in the mosquito vectors of the parasite.[6-9] There is an urgent need for the development of new drugs and vaccines to reverse a progressive resurgence in malaria morbidity and mortality. Better understanding of the malaria parasite biology is essential for the development of new intervention therapies and their efficient use for long-lasting control of this insidious disease.

Application of new technologies has produced a wealth of information in recent years about the genomes, proteomes, and other aspects of the basic composition of the malaria parasites. Many aspects of the parasite's biology can be inferred through these approaches, and yet the ability to utilize this new information to reveal the complex biology of Plasmodium has been slow due, at least in part, to the lack of robust and user-friendly molecular genetic tools. Manipulating the Plasmodium genome has been a great challenge due to the very low efficiency of transfection of this parasite, estimated to be about $10^{-6}$.[10] Gene-targeting to identify gene functions is a cumbersome process hindered by the need to build individual targeting plasmids for each homologous recombination and a lengthy selection process for obtaining genome integrants.[1-4] Further complicating this process in P. falciparum is the tendency of the parasite to maintain extracellular plasmid DNA as stable self-replicating episomal concatamers.[11]

Transposable elements have been widely used as tools to manipulate genomes ranging from different microbes to higher invertebrates, like Drosophila, and even plants. Transposable elements do not occur naturally in many lower eukaryotes, including Plasmodium.[12] Therefore, conditions needed for transposition might be harder to achieve in this parasite. So far, efficient transposon-mediated random mutagenesis in parasitic protozoa has been reported only in Leishmania.[13] There has been a report of transposition in Plasmodium using the Drosophila mariner transposable element, but the transposition events occurred at a very low frequency, without the presence of the transposase, and with only two integrations in the same locus.[14]

The piggyBac transposable element is derived from the cabbage looper moth Trichoplusia ni and is a member of the TTAA-target site-specific class of transposable elements.[15-18] piggyBac is a Class II transposable element that exclusively targets the tetra nucleotide target site, TTAA, and always inserts and excises in a precise manner. piggyBac-based transposon vectors have been widely used to manipulate genomes of various invertebrate species, and piggyBac is currently the preferred vector of choice for enhancer trapping, gene discovery and identifying gene function in Drosophila and other insects.[19-23] The attribute of piggyBac to non-preferentially integrate into the genome of Drosophila has made it more attractive than the P-element, which seems to have preferential hot spots for insertion in 5' regulatory sequences.[19]

A need continues to exist in the art of malarial disease control and molecular biology for a more complete functional analysis of the Plasmodium falciparum genome. However, this work continues to be restricted by the limited ability to effectively and efficiently genetically manipulate this malarial parasite using existing techniques and molecular tools.

SUMMARY

The above and other long-felt needs in the art are met by the present invention.

According to one aspect of the present invention, there is provided a highly efficient method for transforming a disease-transmitting parasite, particularly a parasite that transmits malarial disease. In particular embodiments, the disease-transmitting parasite is Plasmodium falciparum. In particular, the method comprises a transposon-mediated insertional mutagenesis method for transforming a disease-transmitting parasite, such as Plasmodium falciparum, in a method that employs a helper plasmid and a piggyBac transposon construct. In some embodiments, the method employs a lepidopteran transposon construct, particularly a piggyBac transposon as described herein, having a selectable marker or a detectable expressed transgene, for transforming the malarial parasite, Plasmodium falciparum.

In some embodiments, the method employs a piggyBac transposon construct that includes a selectable marker defined as a drug selection marker. By way of example, the drug selection marker may comprise a drug resistance gene, such as human dihydrofolate reductase (hDHFR). In this manner, transformed disease transmitting parasites, such as transformed Plasmodium falciparum, may be selected according to the present method by selecting Plasmodium within a culture that are resistant to the selection drug.

In some embodiments, the method employs a piggyBac transposon construct that includes a detectable expressed transgene defined as a reporter gene that expresses a product detectable visually or at a molecular level, for example, by using methods known to those of skill in the molecular biological arts. By way of example, the reporter gene may comprise a detectable expressed transgene, such as Green Fluorescent Protein (GFP). In this manner, transformed disease transmitting parasites, such as transformed *Plasmodium falciparum*, may be selected according to the present method by selecting *Plasmodium* within a culture that express the detectable transgene product.

In some embodiments, the method provides for preparing transformed disease-transmitting parasites, such as *Plasmodium falciparum*, that possess a relatively large number of TTAA insertion sites. For example, the *Plasmodium falciparum* genome is relatively rich in TTAA insertion sites, having 328,961 insertion TTAA sites, and 159,841 of these TTAA insertion sites being located in the transcriptional units of *P. falciparum*, those parts of genes actively transcribed and translated into proteins or other functional products.

In some embodiments, the method provides for insertional transformation of a disease-transmitting parasite genome at high efficiencies, and at high saturation levels. For example, in some embodiments, the method provides for the transformation of a disease-transmitting parasite genome, such as *P. falciparum*, at an about 40%, 50% or more genome saturation level (about 10,000 mutations in the *P. falciparum* genome). In some embodiments, the saturation level of insertional transposition achieved using the described methods may be 40%, 50%, 60%, 70%, 75%, 80%, 90% or even 100% saturation level in the genome of the particular disease transmitting parasite being transmitted.

The methods of the invention also provide for very stable transformants. In some embodiments, the stable transformants may be described as capable of maintaining the inserted transformational modifications through 20 passages or more, even in the absence of a helper plasmid.

In some embodiments, the efficiency of the insertional mutagenesis achieved using the herein described methods and constructs is about 6.0 to about $13 \times 10^{-4}$.

The number of insertions, and hence the level of insertional genome saturation achieved in a disease-transmitting parasite genome, using the presently described methods and constructs will, of course, vary, with the particular gene, as the number of TTAA potential insertional target sites is known to vary greatly between genes. However, the average number of potential insertional sites, particularly TTAA-targeted insertional sites, is 20 or greater. Hence, the presently described methods provide for efficient and highly saturating insertional transformation of virtually any disease-transmitting parasite that possesses a genome having TTAA regions. In some embodiments, the number of random insertion sites into the *P. falciparum* genome is 10, 9, 8, 7, 6 or 5.

Figure 6:
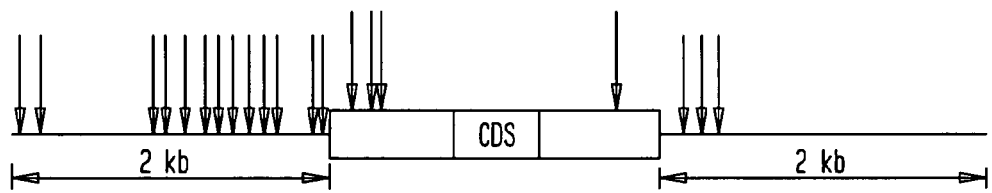

The methods described herein, in some embodiments, provides for the insertional transformation of the *P. falciparum* genome primarily in the 5' untranslated region (UTR), and just after the 5' start site of a gene (See FIG. 6 model, as a representative summary of the distribution of piggyBac insertions relative to the coding sequence (CDS) of *P. falciparum* genes).

In some aspects, the method employs a transposase-expressing helper plasmid in the transformation process/method. In some embodiments, the transposase-expressing helper plasmid is pHTHc-d. In particular embodiments, this helper plasmid is prepared as a modified pHTH helper plasmid that has been replaced with the calmodulin promoter, and the *P. falciparum* dhfr promoter is inserted head to head to the calmodulin promoter in an inverted arrangement (See FIG. 5, middle panel). The helper plasmid is preferably designed so as to boost or increase transposase expression when used in the presently described methods for transforming a disease-transmitting parasite, such as in the transformation of the malarial disease transmitting parasite, *Plasmodium falciparum*. In other embodiments, the helper plasmid is described as comprising a selectable marker. In some embodiments, the selectable marker is BSD (helper plasmid designated pHTH-BSD) or NEO (helper plasmid designated pHTH-NEO).

In some aspects, the invention provides a lepidopteran transposon construct. In some of these embodiments, the lepidopteron transposon is piggyBac. In some embodiments, the lepidopteran transposon construct includes a selectable marker. In some of these embodiments, the selectable marker is a drug resistance gene, such as human dihydrofolate reductase (DHFR). In particular embodiments, the drug selection cassette includes a hrp3 promoter. In specific embodiments, the drug selection cassette (that includes these substitutions and modifications) is pXL-BACIII-hDHFR. (See FIG. 5, bottom panel).

In another aspect, the invention provides for a molecular model that may be used to identify a gene of interest using a non-specific targeting strategy. This strategy, in some embodiments, relies on phenotype for selection, and employs a lepidopteron transposon construct described as a promoter trap plasmid. In some embodiments, the promoter trap plasmid employs a design wherein the 5' untranslated region (UTR) regulatory sequence of the construct is truncated and abrogates expression of the selectable marker gene contained therein, such as the selectable marker gene hDHFR. In some embodiments, the selectable marker gene hDHFR is obtained from the plasmid pXL-BACIII-DHFR. (See FIG. 7, minimal promoter trap plasmid design). This simple promoter trap strategy relies on an indigenous promoter located upstream of the transposon insertion for expression. With this strategy, the drug selectable marker has a promoter-less drug selection cassette. This strategy permits the functional annotation of a gene using, for example, the piggyBac construct to achieve insertional mutagenesis (transformation) in *Plasmodium falciparum*, for the characterization of virtually any gene of interest in this lepidopteron disease-transmitting parasite. This provides a powerful molecular tool for further characterizing and manipulating the genome of this parasite, as well as providing a potential screening tool for the characterization and selection (screening) of libraries of potential molecular based anti-malarial agents. This strategy permits the identification of genes and regulatory networks that are potential targets for drug, vaccine, and other intervention strategies to prevent and control malaria.

By way of example, the promoter trap plasmid design may be prepared with a reporter gene of choice. By way of example, such a reporter gene may comprise green fluorescent protein (GFP) (See FIGS. 9 and 10). Other reporter genes include that express a product detectable using methods common to the field of research, such a chloramphenicol acetyl transferase (CAT), luciferase (LUC), chloroquine resistance (pfcrt), red fluorescent protein (RFP), blue fluorescent protein (BFP), yellow fluorescent protein (YFP), hemagglutinin epitope (HA), and c-MYC epitope. In some embodiments, the promoter trap plasmid is placed in the plasmid pXL-BACIII-DHFR. In this particular promoter trap plasmid, the GFP open reading frame (ORF) is placed in the plasmid pXL-BACIII-DHFR without a functional promoter, having only part of the 5' untranslated region (UTR) lacking the transcription start site. In this construct, the drug resistance cassette is independent of the promoter trap reporter. In some embodiments, the GFP expression occurs when the transposon inserted at a position adjacent to a promoter. This model also provides a method for functionally annotating *Plasmodium* genes using a non-specific targeting strategy combined with a selection method that employs an introduced transgene marker.

In another aspect, the invention provides a method to evaluate *Plasmodium* genes and proteins that are putative vaccine targets by inserting these targets (or any one of these targets) as transgenes into the *Plasmodium* genome. In this particular transgene plasmid, the open reading frame (ORF) of a target gene, such as the vaccine candidate Merozoite Surface Protein-1, Erythrocyte Binding Protein-175, Apical Membrane Antigen-1, or *Plasmodium vivax* Duffy Binding Protein, may be placed in a piggyBac plasmid, such as pXL-BACII-DHFR, with a functional promoter and other regulatory sequences sufficient to express the target protein during parasite development. (See, e.g., FIG. 11) Such a promoter may be the native gene promoter to replicate gene expression of the native gene or another promoter to express the target gene at different quantities or at different times during parasite development. In this manner, natural and artificial variants of the target gene and the target product can be evaluated for their sensitivity to anti-malarial immunity.

In yet another aspect, the invention provides a vaccine comprising the identified *Plasmodium* genes and/or proteins identified and selected as useful for providing anti-parasite protection (i.e., as an anti-malarial), these genes and/or proteins being identified according to the method identified above.

The invention may also comprise a composition having an enriched concentration of attenuated transformed parasites, said attenuated transformed parasites comprising an orphan fragment of the piggyBac element. In some embodiments, the attenuated transformed parasites are *Plasmodium falciparum.*

In another application, the invention provides a method to evaluate *Plasmodium* genes and proteins that are the putative drug targets by inserting these targets as transgenes into the *Plasmodium* genome. In some embodiments, the open reading frame (ORF) of a target gene of a particular transgene plasmid, such as a gene for drug resistance, may be pfmdr, pfcrt, or dhfr. The target gene may be placed in a piggyBac plasmid, such as pXL-BACII-DHFR, with a functional promoter and other regulatory sequences sufficient to express the target protein during parasite development. Such a promoter may be the native gene promoter to replicate gene expression of the native gene or another promoter to express the target gene at different quantities or at different times during parasite development. Drug resistance genes of *Plasmodium vivax* and other related organisms may be evaluated similarly. In this manner, natural and artificial variants of the target gene for drug resistance can be evaluated for their sensitivity to anti-malarial drug action. Regulating factors and modifying traits associated with such drug resistance may be identified by introduction of such transgenes into different parasite genotypes.

In another aspect, the invention provides for a method to inactivate a gene permanently. In this method, the plasmid design has an asymmetric arrangement of inverted repeat (ITR) elements, for example two tandem 5' ITR and one 3' ITR, such that in the presence of the transposase, a single ITR element remains inserted in the genome when the functional parts of the piggyBac element are mobilized (FIG. 12). While not intending to be limited to any particular theory or mechanism of action, it is proposed that this method may permit gene inactivation by disruption of the open reading frame or the promoter regions using 'spacer' DNA. Other plasmid designs of these embodiments of the construct may insert an additional DNA element directly into the open reading frame of the gene to fuse another protein element with the gene target, using a reporter gene open reading frame such as GFP or HA3. Through this method, genes may be modified or inactivated singly or multiply to create attenuated parasites to be used as a vaccine.

In yet another aspect, the invention provides for a method of codon optimization of the piggyBac trasposase. In this codon optimization method, the open reading frame (ORF) of piggyBac transposase, which has 50 rare codons compared to the *P. falciparum* codon sequence, is modified to include replacements codons that are common to *P. falciparum*. In the analysis of the piggyBac ORF region, it was determined that these rare codons occurred at every third base, and therefore, every third base of the piggyBac codon sequence will be replaced with the replacement codons identified in Table 2. In this manner, codon optimization may be achieved, and optimal expression in the organism of interest, such as the *P. falciparum*, may be achieved. The native ORF sequence for piggyBac appears in Table 3.

BRIEF DESCRIPTION OF THE DRAWINGS

The invention will be described in conjunction with the accompanying drawings, in which:

FIGS. 1A-1C provide a plasmid design and procedure for piggyBac transformation of *P. falciparum*. (FIG. 1A) pXL-BACII-DHFR, a piggyBac transposon vector for transformation of *P. falciparum*, was created by cloning the human dhfr coding sequence under the control of 5' calmodulin and 3' histidine rich protein-2 into the minimal piggyBac vector pXL-BACII. The human dhfr cassette was excised from the vector pHH1 as a 2.2 kb EcoR I/Bgl II fragment and cloned into pXL-BacII such that it is flanked by the piggyBac inverted terminal repeats (ITR 1, ITR 2). (FIG. 1B) The pHTH helper plasmid was constructed by cloning the piggyBac transposase coding sequence under the control of *P. falciparum* 5' and 3' heat shock protein 86 sequences. piggyBac transposase expressed in the blood stages of *P. falciparum* will catalyze the transposition of the piggyBac element from the vector pXL-BACII-DHFR into the *P. falciparurn* genome. (FIG. 1C) Schematic representation of the procedure used to transform *P. falciparum*. Mature blood-stage parasites were purified by passage through a magnetic column (Miltenyi Biotec) and reintroduced into culture with erythrocytes preloaded by electroporation with plasmids pXL-Bac11-DHFR and pHTH. After 1-4 generations of growth in the preloaded erythrocytes, parasites were selected with 2.5 nM WR9921 0 until drug-resistant parasites emerged in culture.

FIGS. 2A and 2B present a confirmation of piggyBac integration into the *P. falciparum* genome. (FIG. 2A) Parasite genomic DNA was digested with EcoR I, and Southern blot hybridization using a human dhfr probe identified unique piggyBac hybridization bands from parasites co-transfected with pXL-BACII-DHFR and pHTH. In studies 1 and 2, parasites (*P. falciparum*) were transfected with plasmids pXL-BACII-DHFR and pHTH, in 1:1 and 2:1 ratios, respectively, and the parasites were maintained for one generation in plasmid-loaded erythrocytes before selection with WR99210. In other studies (3-8), parasites were transfected with the plasmids in a 2:1 ratio and maintained in culture for four generations before selection with WR99210. Transfections for studies 1, 2, 7, and 8 were initiated in a 5 ml culture volume and in experiments 3-6 transfections were performed in 200 μl cultures in a 96-well plate. After Southern blot hybridization, the episomal band was seen as a 6.2 kb fragment. The identified piggyBac integrations are indicated by letters. (FIG. 2B)

Southern blot hybridization analysis of individual clones obtained from populations "1" and "2" identified clones with different sites of integrations. Clones A1, B8, B12, C8 and F4 appear to have the common insertion "a" and are likely to be of the same origin. Clone B4 and G5 have dissimilar sites of integration, "b" and "c".

Figure 3:
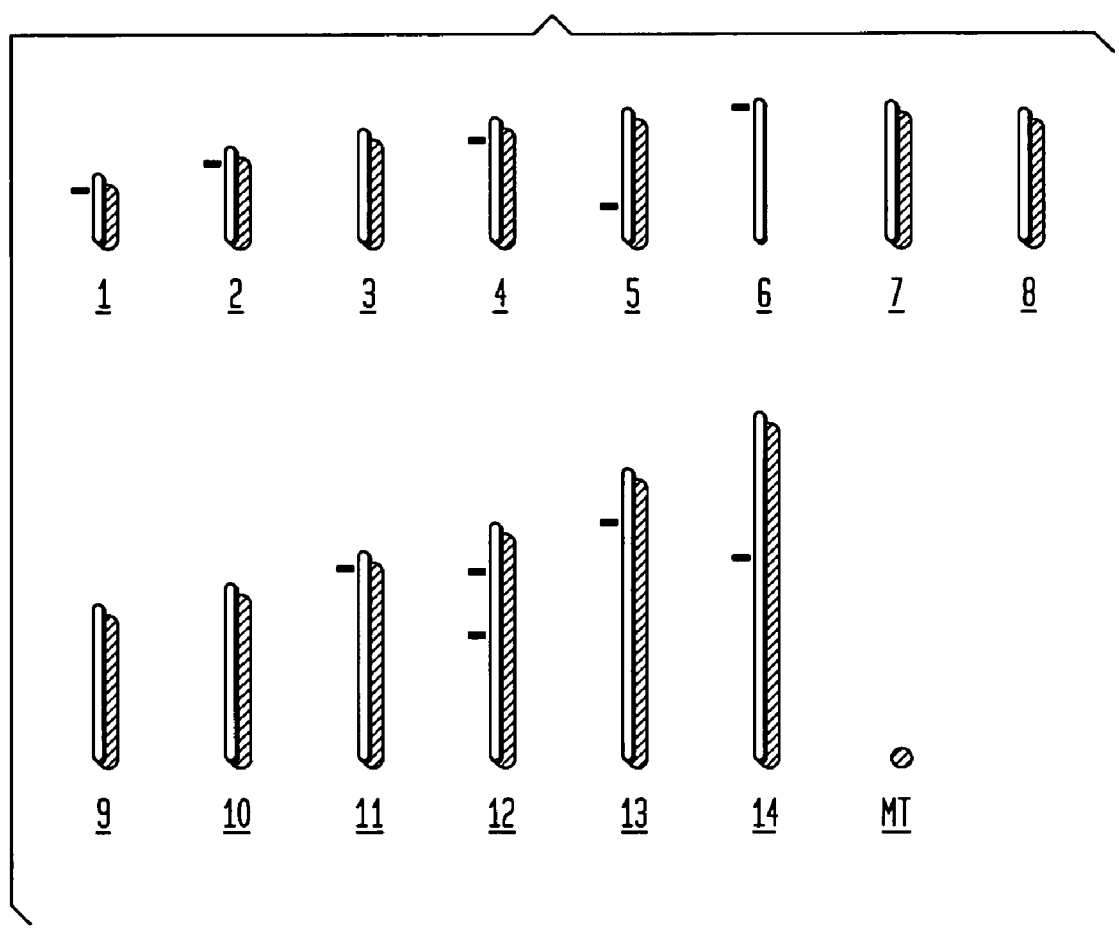

FIG. 3 is a representation of piggyBac insertions in the *P. falciparum* genome. A mapview of piggyBac insertions in the *P. falciparum* chormosomes shows a genome-wide distribution.

FIG. 4 presents the identification of integration sites into the P. falciparum genome. Inverse PCR analysis was used to identify the piggyBac 5' terminal repeat (TR) insertion sites. Briefly, genomic DNA for drug-resistant populations were digested with either Sau3A I or Rsa I and self-ligated in a dilute reaction. Sau3A I self-ligated fragments were then digested with Tse I to remove the episomal fragment. The remaining self-ligated fragments were then used as a template in an inverse PCR reaction to identify sites of integration into the genome. Sequence analysis identified nine different sites of integration in eight different chromosomes, suggesting a genome-wide insertion of piggyBac. The piggyBac element had inserted in a TTAA target sequence in all the analyzed clones. PCR analysis was then performed using a genomic primer at each insertion site and a primer in ITR1 to confirm that the insertion of the piggyBac element was complete. Further sequence analysis confirmed the insertion of piggyBac ITRs into a "TTAA" target sequence that resulted in the duplication of the target site in the genome. The italicized sequences in insertions "b", "g", "h" and "I" were not confirmed by sequencing. Instead, the insertion of the ITR1 in those populations was confirmed by Southern blot hybridization analyses (SEQ ID NOS: 3-20 are disclosed respectively in order of appearance).

Figure 5:
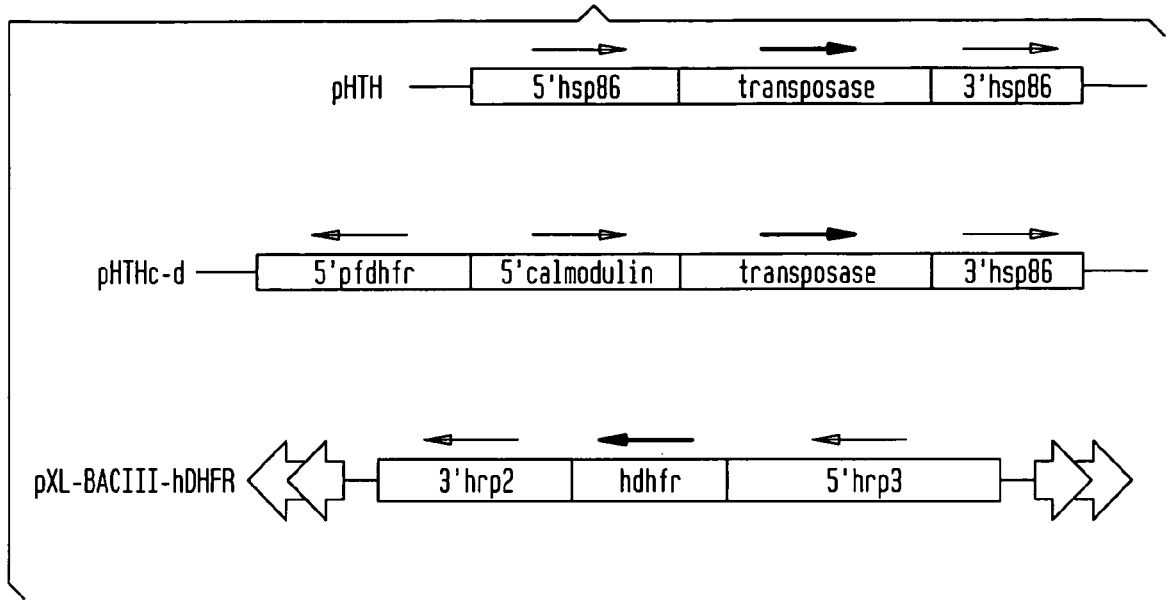

FIG. 5 presents the hsp86 promoter of the helper plasmid pHTH and helper plasmid pHTHc-d with the 5' hsp86 promoter replaced with the calmodulin promoter and *P. falciparum* dhfr promoter inserted head to head in an inverted arrangement. The 5' calmodulin promoter of the drug selection cassette of pXL-BACII-hDHFR may be replaced with the 5' hrp3 promoter to create pXL-BACIII-hDHFR. Arrows indicate the orientation of the gene elements in relation to the ORF of the gene (e.g., hDHFR).

FIG. 6 presents a summary of the distribution of piggyBac insertions in the *P. falciparum* genome with respect to coding sequence (CDS).

Figure 7:
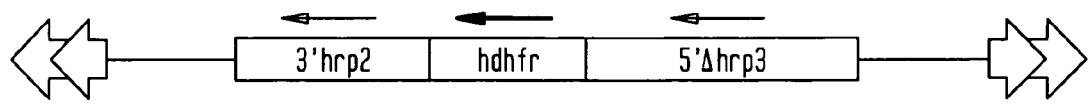

FIG. 7 presents a minimal promoter trap plasmid design. The 5'UTR regulatory sequence was truncated to cause abrogated expression of hDHFR from the plasmid pXL-BACII-DHFR.

Figure 8:
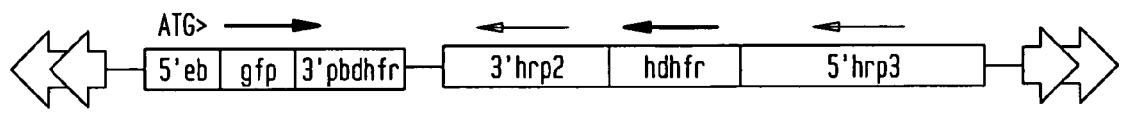

FIG. 8 provides an example of a piggyBac element with a hDHFR selection cassette and a GFP reporter.

Figure 9:
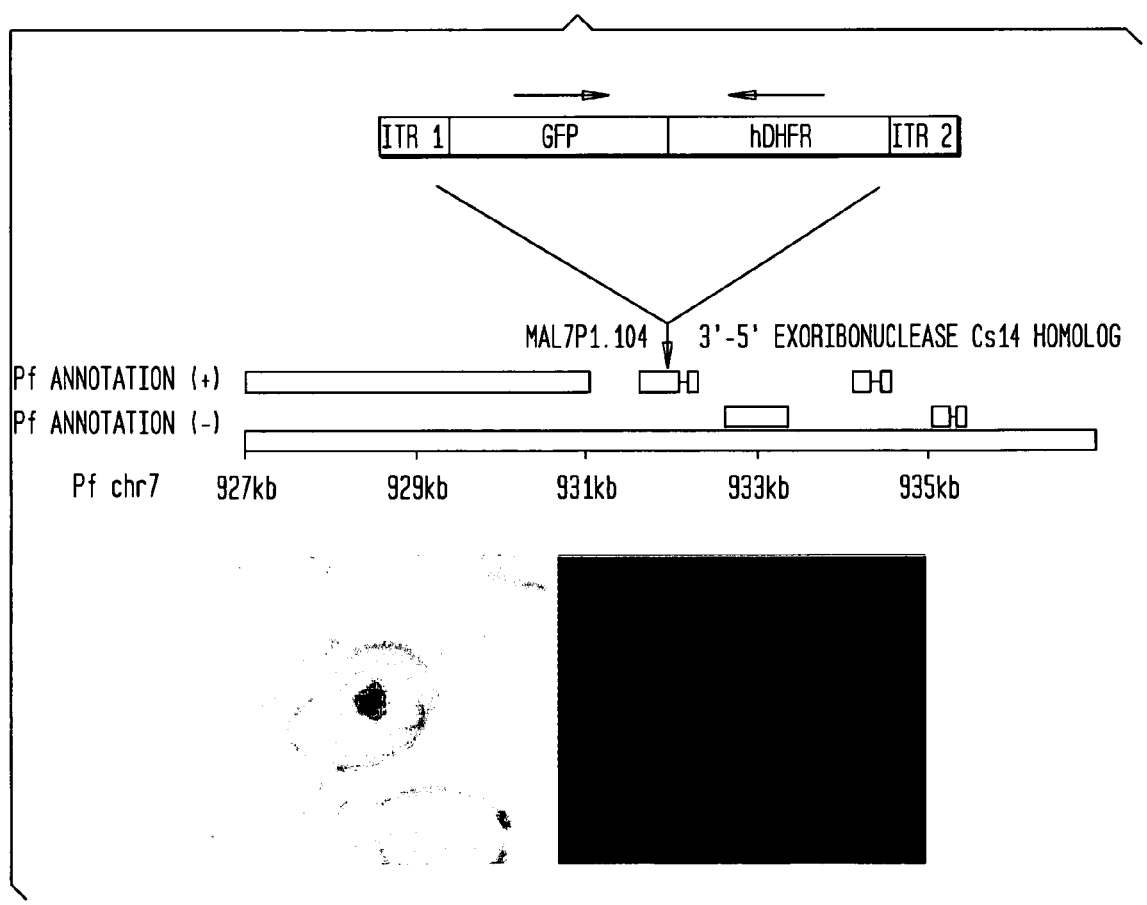

FIG. 9 presents a promoter trap plasmid design with a GFP reporter. The GFP ORF is placed in the plasmid pXL-BACII-DHFR without a functional promoter, having only part of the 5'UTR lacking the transcription start site. The drug resistance cassette is independent of the promoter trap reporter. GFP expression occurred when the transposon inserted adjacent to a promoter. This application establishes the utility of piggyBac to be used for functional annotation of *Plasmodium* genes using a non-specific targeting strategy, combined with a selection method using an introduced transgene marker.

Figure 10:
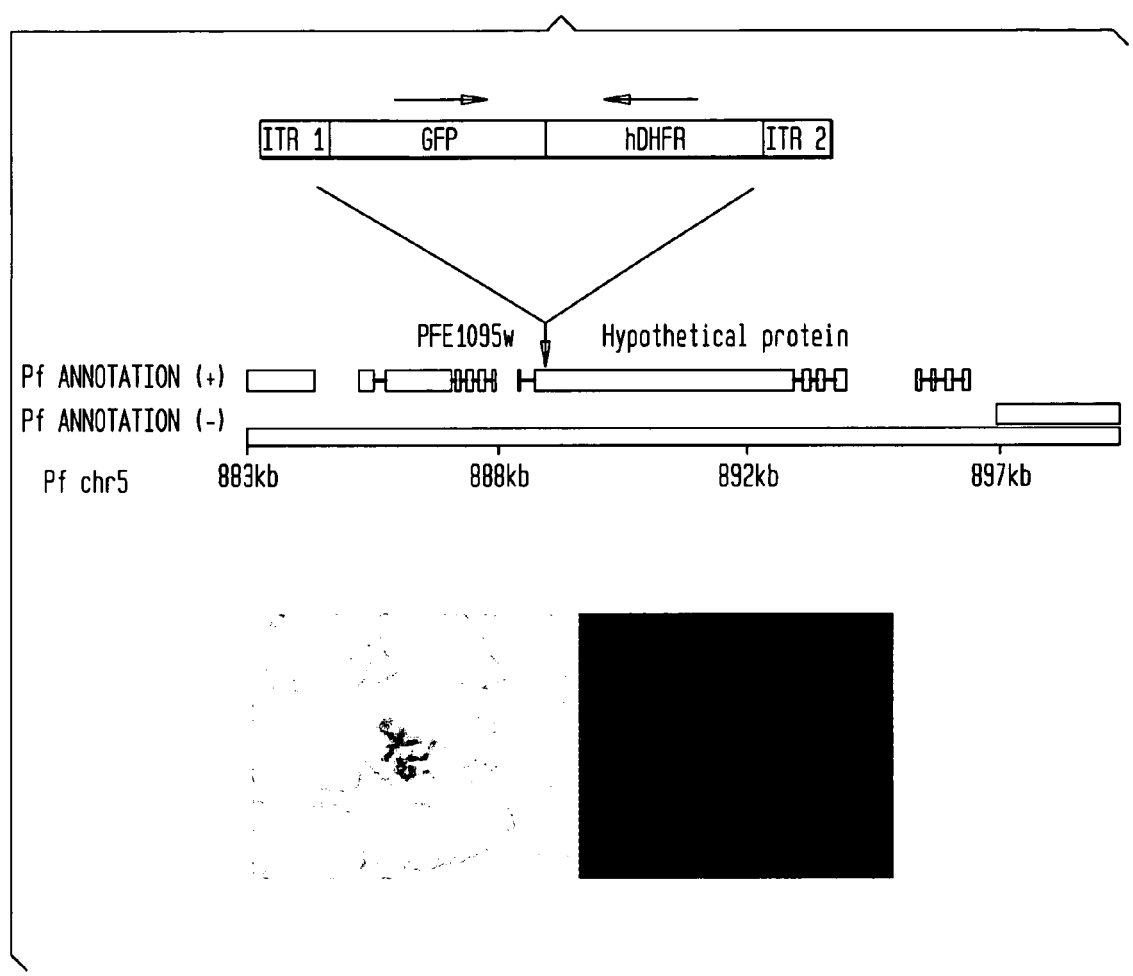

FIG. 10 presents results from promoter trap studies showing GFP expression from the introduced transgene construct inserted into the *Plasmodium* genome by the piggyBac element.

FIG. 11 presents an example of a transgene design in piggyBac to express a target gene of a vaccine candidate, *Plasmodium vivax* Duffy Binding Protein.

FIG. 12 presents an example of an asymmetric arrangement of inverted terminal repeat (ITR) elements to be used to inactivate genes or create a direct fusion of open reading frames of an introduced gene and a *Plasmodium* gene.

DETAILED DESCRIPTION

It is advantageous to define several terms before describing the invention. It should be appreciated that the following definitions are used throughout this application.

DEFINITIONS

Where the definition of terms departs from the commonly used meaning of the term, applicant intends to utilize the definitions provided below, unless specifically indicated.

For the purposes of the present invention, the term "spacer" refers to sequences, for example from 3 base pairs (bp) to about 31 base pairs (bp) or more in length, separating the 5' and 3' (respectively) terminal repeat and internal repeat sequences of the piggyBac transposon.

For the purposes of the present invention, the term "vector" refers to any plasmid containing piggyBac ends that is capable of moving foreign sequences into the genomes of a target organism or cell.

For the purposes of the present invention, the term "plasmid" refers to any self-replicating extrachromosomal circular DNA molecule capable of maintaining itself in bacteria.

For the purposes of the present invention, the term "transgenic organism" refers to an organism that has been altered by the addition of foreign or introduced DNA sequences (i.e., not naturally occurring or native DNA sequence and/or inserted at a new (non-native site) chromosomal location) in to its genome.

For the purposes of the present invention, the term "genetic construct" refers to any artificially assembled combination of nucleic acid, including DNA and/or RNA, sequences.

For the purposes of the present invention, the term "helper construct" refers to any plasmid construction that generates the piggyBac transposase gene product upon transfection of cells or injection of embryos.

For purposes of the present invention, the term "cell" referres to any eukaryotic or prokaryotic cell capable of being genetically manipulated from its native, wild type genetic content.

DESCRIPTION

The methods of the present invention provide for more highly efficient and predictable techniques for manipulating and using the lepidopteron transposon derived piggyBac for the transformation and study of disease transmitting parasites, as well as the diseases that are manifest by these parasites.

EXAMPLES

The following non-limiting examples are illustrative of the present invention, and should not be construed to constitute any limitation of the invention as it is described in the claims appended hereto.

Example 1

High Transformation Efficiency of *P. Falciparum* Using PiggyBac Method

The present example demonstrates the utility of the present invention for use as a highly efficient method for transforming disease transmitting parasites, such as *P. falciparum*, using the piggyBac constructs and a helper plasmid as defined herein. These methods provide a *P. falciparum* transformation technique that is at least 100 times more efficient than those previously available.

A minimal piggyBac transposon vector, pXL-BACII-DHFR, was created by cloning the human dihydrofolate reductase (hdhfr) coding sequence under the control of *Plasmodium* 5' and 3' regulatory elements of calmodulin and histidine rich protein-2, respectively, in the plasmid vector, pXL-BACII.[24] This drug resistance cassette was flanked by the 3' inverted terminal repeat (ITR1) and the 5' inverted terminal repeat (ITR2) of the piggyBac element (FIG. 1A). The ITRs are oriented such that, upon transposition, they will carry the drug-resistance cassette into the *Plasmodium* genome without any of the plasmid backbone.

Figure 1B:
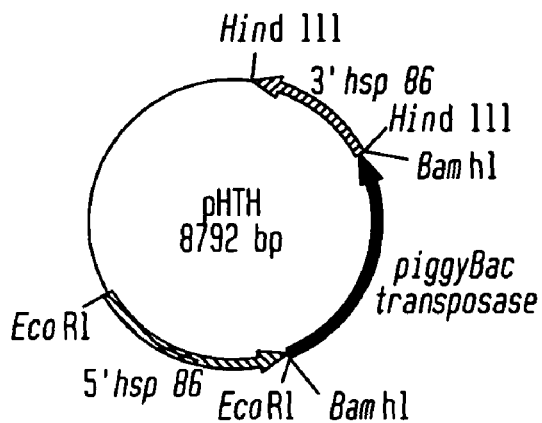

A helper plasmid, pHTH, was created by cloning the piggyBac transposase coding sequence under the control of heat shock protein 86 (hsp 86) regulatory elements to mobilize the piggyBac element in the erythrocytic stages of *P. falciparum* (FIG. 1B). Intended only for transient transfection, this helper plasmid contained no selectable marker.

Figure 1C:
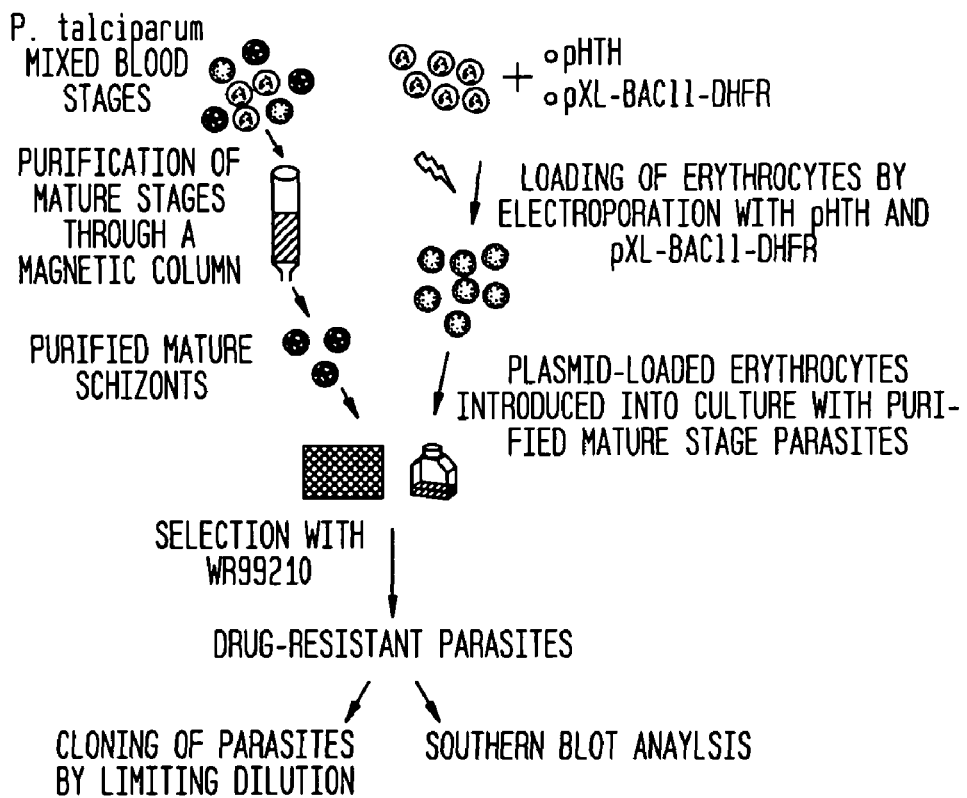

Mature blood-stage *P. falciparum* NF54 parasites were purified by isolation on a magnetic column (Miltenyi Biotec). The paramagnetic hemozoin (heme polymer) present in the food vacuole of the parasites allows the separation of parasitized erythrocytes from the uninfected erythrocytes.[25] The purified parasitized erythrocytes were then cultured in RBCs loaded with plasmids pXL-BACII-DHFR and pHTH[26] (FIG. 1C). Purification through the magnetic column ensured invasion of only DNA-loaded erythrocytes, whereupon parasites spontaneously acquired plasmids from the erythrocytes.[26]

Figure 2A:
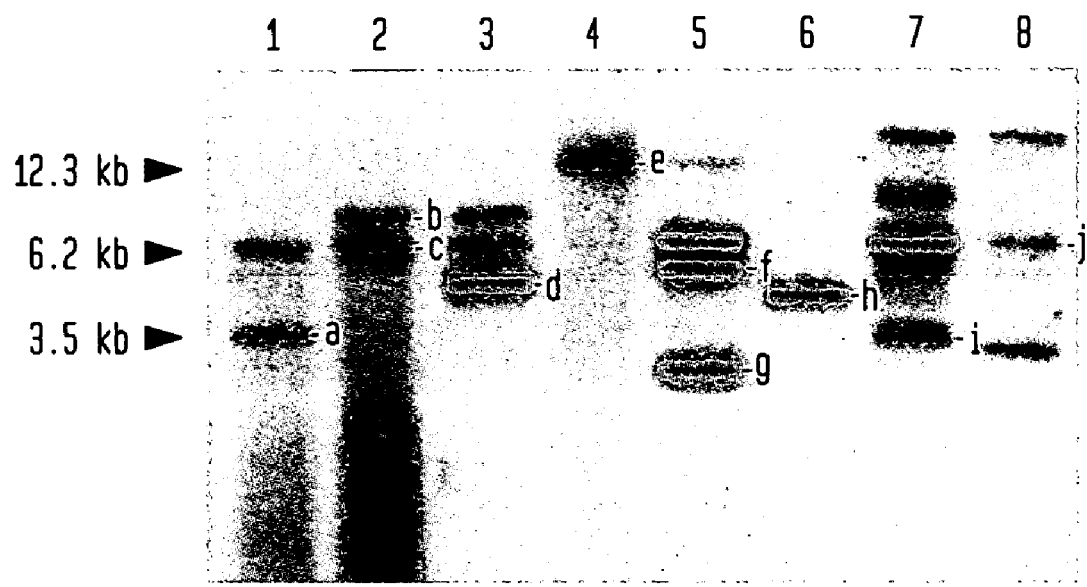

After 1-4 generations of parasite growth in DNA-loaded erythrocytes, WR99210 was used to select parasites expressing hDHFR. Drug-resistant parasites were obtained from eight different transfected cultures, and Southern blot hybridizations were performed using an hdhfr probe. Novel hybridization bands were detected in each parasite population, in addition to the episomal band, indicating multiple unique integrations of the piggyBac element into the *P. falciparum* genome (FIG. 2A).

The average transformation efficiency of piggyBac was estimated from eight independently transfected parasite populations to be $6.4-12.6 \times 10^{-4}$ (Table 1). This transformation efficiency is approximately 100 times more than what has previously been reported for *Plasmodium*.[10] There was no evidence for piggyBac insertions in the absence of the helper plasmid.

Example 2

Stability of PiggyBac-Transformed *P. Falciparum*

The present example demonstrates the utility of the present invention for providing stable genetically modified malarial parasites, *Plasmodium falciparum*, that was achieved using the piggyBac construct defined herein in the presence of a helper plasmid. The transformed *P. falciparum* were stable for at least 20 generations in the absence of a helper plasmid. The present example also demonstrates the utility of the method for providing multiple random insertions into the *P. falciparum* genome using the piggyBac constructs in the presence of a helper plasmid.

Figure 2B:
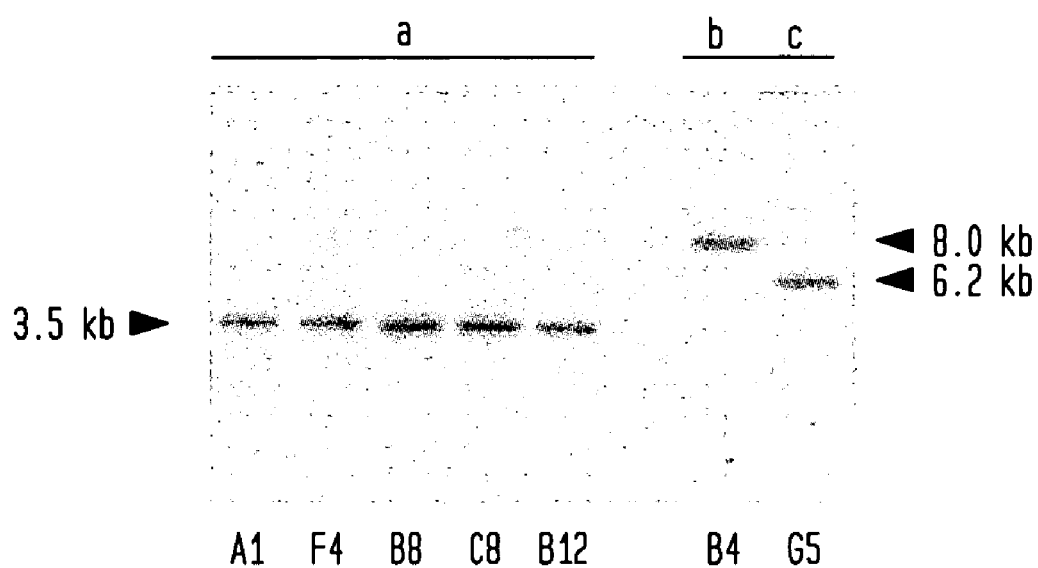

In order to test the stability of piggyBac integrations in the genome, parasites from populations "1" and "2" were cloned by a limiting dilution method.[27] Southern blot hybridizations with an hdhfr probe identified clones with integrations into the genome. Clones A1, B8, B12, C12 and F4 derived from population "1" appeared to have the same integration, "a", while clones B4 and G5 that were derived from population "2" had two different integrations, "b" and "c" (FIG. 2B).

These clones were maintained in culture for 20+ generations in the absence of the helper plasmid. The integrated piggyBac cassette was stable in all the clones as seen by Southern blot hybridizations. Hence, there was not any endogenous transposase activity.

Example 3

Multiple Site Transformation of *P. Falciparum* Genome Using PiggyBac Construct Method The present example demonstrates the utility of the present invention for providing multiple, random insertions into a *P. falciparum* genome.

To identify the sites of integration in the transformed populations, inverse PCR analyses were performed at the ITR2 of piggyBac[28]. The inverse PCR products were then cloned into the pGEM T-easy vector (Promega) and sequenced.

From the multiple integrations obtained in the transformed populations, nine (9) different insertion sites were isolated and identified. These insertions represented the predominant population in each transfection study, and therefore were identified with ease (FIG. 2A). The nine (9) identified insertions were dispersed in different chromosomes throughout the genome of the parasite (FIG. 3). Sequence analysis of these nine insertions confirmed a consensus TTAA-site specific integration of the piggyBac element into the parasite genome, as expected for authentic transposition (FIG. 4).

Integration of the ITR1 of the piggyBac element was confirmed in separate PCR reactions using locus-specific primers and a primer in the ITR1 of piggyBac. Sequence analysis confirmed the TTAA duplication at the ITR1 end of the insertion for all integrations, except for integrations "b", "g", and "h" due to the AT-rich repeat regions in those sequences. Instead, the complete integration of the DHFR cassette was confirmed in these populations by Southern hybridization RFLP analysis.

All of the identified piggyBac integrations occurred outside of the predicted ORFs,[29-30] except for integration "b" which had the insertion approximately 100 bp downstream of the start codon of a hypothetical Asparagine-rich protein (PFD0200c), thereby disrupting the putative ORF of this gene.

Five insertions, "c", "f", "g", "h", and "i" were in the 5' region of the closest ORFs. Insertions "c", "i" and "j" were located approximately 1000 bp 5' to the nearby ORF. Insertions "f" and "g" were approximately 300 bp upstream, respectively. Insertions "a", "d" and "e" were 100 bp, 150 bp and 465 bp downstream of the closest ORFs, respectively. Further analysis will characterize the effects of these insertions on gene expression in these transgenic parasite-lines.

Based on the distribution of these piggyBac integration sites in the non-coding regions, it is not clear whether this apparent bias is significant. Given the higher AT richness of the non-coding regions (86%) of *P. falciparum* verses its coding regions (74.2%), such an apparent bias may reflect a greater probability of a TTAA target for piggyBac insertion occurring in the noncoding regions. Also, *P. falciparum* has a low gene density with long intergenic regions, which could increase the chances of insertions occurring in the intergenic regions.

Example 4

TTAA-Rich Target Sites in *P. Falciparum* for PiggyBac Integration

The present example demonstrates the high distribution of TTAA sites in the *P. falciparum* genome, and the amenability of these sites for manipulating the *P. falciparum* genome using these sites as targets for genetic integration using the piggyBac transformation system and helper plasmid. The pattern of this distribution of TTAA target sites in the *P. falciparum* genome is also identified in the present example. The present example also demonstrates the utility of the piggyBac-transformation system as a useful tool in large-scale genetic screening protocols.

183,422 (59.5%) of TTAA sites were found in the noncoding regions of the *P. falciparum* genome, and 124,733 (40.5%) of TTAA sequences were found in the EST sequences of *P. falciparum*. From this, approximately five targets in each *P. falciparum* gene were identified.[29,30] The identification of these multiple TTAA sites provided a mechanism for transforming *P. falciparum* at an extremely high efficiency.

TABLE 1 piggyBac transformation efficiency in *P. falciparum*

| Protocol | Parasite number | Generations in loaded RBCs | Insertions obtained | Transformation Frequency |
|---|---|---|---|---|
| A | $4 \times 10^5$ | 1 | 3 | $7.5 \times 10^{-6}$ |
| B | $2 \times 10^5$ | 4 | 8 | $4 \times 10^{-5}$ |
| C | $8 \times 10^3$ | 4 | 9 | $1.1 \times 10^{-3}$ |

Using an hdhfr-tagged piggyBac transposon, a transgenic *P. falciparum* population was generated by bonafide transpositional integration into the genome, in the presence of a transposase-expressing helper plasmid. Insertions were obtained randomly throughout the *P. falciparum* genome at high transformation efficiency, and the genomic insertion sites were rapidly identified by using an inverse PCR technique.

Parasites with single transposon insertions were cloned out from mixed populations and the integrated transposons in these transformed parasite lines were stable for many generations, thus confirming their utility for phenotypic analyses.

piggyBac-mediated transformation protocols were adapted for conditions compatible for large-scale genetic screening, further corroborating the tremendous utility of this technique. The practicality of such a useful application was demonstrated by the transfected parasite populations 3-6 (FIG. 2A), which were transformed in a 96-well microtiter plate. Multiple integrations occurred in these small parasite populations, thereby achieving very high transformation efficiencies. This demonstration of the ability to transform *P. falciparum* with relative ease and high efficiency, by using only a few thousand parasites in a small culture volume, confirmed the suitability of piggyBac to be used for large-scale genetic screens.

The piggyBac transposition system is demonstrated to be an important new genetic tool for manipulation of the *P. falciparum* genome. This is the first report of high efficiency transposition in this deadly human pathogen. With this efficient integration system, many genetic strategies that have eluded *Plasmodium* research will now be feasible. This methodology, being used in the blood stages, is unable to modify genes that are absolutely essential for the blood-stage development of the parasite. To overcome this, piggyBac mobilization can be carried out in the other life cycle stages of the parasite by using a helper plasmid designed for sexual stage-specific expression with another selectable marker.

The ability of the piggyBac transposable system for use in large-scale mutagenesis of *P. falciparum*, will provide new insight into the complex genetic structure of the malaria parasite and greatly accelerate efforts to develop novel intervention strategies.

Example 5

Helper Plasmid Redesign

The present example describes an efficient helper plasmid that may be used in the practice of the herein described transformation methods using the piggyBac transposon construct.

In some initial studies, the pfhsp86 promoter was used to drive transposase expression in *P. falciparum*. This promoter was chosen because it is known to be effective for transgene expression in transfected *P. falciparum*.

This helper plasmid has been re-engineered to boost transposase expression (FIG. 5) using a 'head-to-head' arrangement of the calmodulin 5'UTR with other promoters to significantly enhance transgene expression. This design may be used to boost transposase expression from the helper plasmid, reinforcing the principle that mobilization of piggyBac can be regulated temporally and quantitatively by altering the noncoding regulatory sequences flanking the piggyBac ORF. As an example, the strong calmodulin promoter is inserted in place of the hsp86 promoter of pHTH and *P. falciparum* dhfr promoter is inserted upstream of the calmodulin 5'UTR in an inverse or head-to-head orientation. This arrangement of promoters can generate substantially higher reporter gene expression levels than plasmid constructs with only a single promoter.

This design of the helper plasmid may be further modified by addition of a selectable marker BSD (pHTH-BSD) or NEO (pHTH-NEO) in order to create a helper line of parasite that constitutively expresses transposase, carrying the helper plasmid as a stable episome. Mobilization of piggyBac in other development stages may be achieved by addition of a stage-specific promoter in place of hsp86 in the pHTH as well as a drug resistance cassette.

Example 6

High Saturation Transformation of *P. Falciparum* with TTAA-Rich Genome

The present example is presented to demonstrate the utility of the present invention for providing a transformation system for a disease-transmitting parasite, such as *Plasmodium falciparum*, that provides a population of transformed *P. falciparum* having a highly saturated transformed genome.

In *P. falciparum*, the total number of target TTAA insertion sites is 328,861 with 159,841 in the CDS. Although the number of TTAA sites per gene varies considerably, the average number of TTAA sites per gene is >20. The pattern of piggyBac insertions within *P. falciparum* genes occur primarily in the 5'UTR and just after the 5' start site (FIG. 6). It is expected that 10,000 mutations will represent about 50% saturation of the *P. falciparum* genome. Higher saturation levels will become progressively less efficient as redundant mutations occur and as multiple TTAA in the same locus are hit. The tendency to target the 5' regions of genes facilitates targeting designs for functional annotation of malarial genes, using promoter trap experiments (FIG. 7) or N-terminal exon trapping of insertional tagging.

High saturation mutagenesis may be used to demonstrate genes essential for parasite development in humans, genes vital for parasite survival, etc.

Example 7

Promoter-Trap Model

The present example is presented to demonstrate the utility of the present invention for use as a technique to annotate a genome of a parasite, such as the malarial parasite, *P. falciparum*, using the herein described piggyBac constructs and helper plasmid technique.

A simple promoter trap strategy was used that relied solely on an indigenous promoter upstream of the transposon insertion for expression (FIGS. 8, 9 and 10). The drug selectable marker had a promoter-less drug selection cassette. This design was sufficient to isolate parasites transformed with this transposable element, establishing our ability to identify genes of interest through non specific targeting strategies that rely on a phenotype selection.

Example 8

Modified "Rare Codon" PiggyBac Construct

The present example is provided to demonstrate the utility of the invention for providing an optimized piggyBac transformation vector that includes substituted codons. These substituted piggyBac constructs have enhanced transformation efficiency potential for transforming the *P. falciparum* genome.

piggyBac transposase has a single open reading frame (ORF) of 1785 nucleotides, and our analysis found that 50 of its 594 codons are rare codons for *P. falciparum*. Rare codons were defined as occurring in ≦10% of the all *P. falciparum* ORFs.[29] Table 2 identifies the amino acids having rare *P. falciparum* codons present in the piggyBac transposase and the more common codon that will be used to replace the native piggyBac nucleotide. In all cases, it is the third base that is replaced. Codon usage in the rodent malaria parasites is similar. Codon optimization provides optimal expression in the organisms of interest.

TABLE 2

| rare codon a.a. | # | replacement codon |
|---|---|---|
| G | 2 | GGA |
| I | 9 | ATA |
| P | 9 | CCA |
| S | 14 | AGT |
| T | 9 | ACA |
| V | 7 | GTA |
| TOTAL = | 50 (≈8.4%) | of transposase CDS |

Example 9

PiggyBac Native Sequence Open Reading Frame

The present example presents the native sequence of the open reading frame (ORF) of the piggyBac transposon. Particular identified "rare codons" within this sequence, rare relative to *P. falciparum* naturally occurring codons, are identified (See Table 2) and replaced so as to provide the modified piggyBac construct having improved efficiency as described in Example 8.

TABLE 3 piggyBac ORF Sequence Range: 1 to 1785 (SEQ ID NO: 1)

```
                15                      30                      45
ATG GGT AGT TCT TTA GAC GAT GAG CAT ATC CTC TCT GCT CTT CTG
 M   G   S   S   L   D   D   E   H   I   L   S   A   L   L>

60                      75                      90
CAA AGC GAT GAC GAG CTT GTT GGT GAG GAT TCT GAC AGT GAA ATA
 Q   S   D   D   E   L   V   G   E   D   S   D   S   E   I>

105                     120                     135
TCA GAT CAC GTA AGT GAA GAT GAC GTC CAG AGC GAT ACA GAA GAA
 S   D   H   V   S   E   D   D   V   Q   S   D   T   E   E>

150                     165                     180
GCG TTT ATA GAT GAG GTA CAT GAA GTG CAG CCA ACG TCA AGC GGT
 A   F   I   D   E   V   H   E   V   Q   P   T   S   S   G>

195                     210                     225
AGT GAA ATA TTA GAC GAA CAA AAT GTT ATT GAA CAA CCA GGT TCT
 S   E   I   L   D   E   Q   N   V   I   E   Q   P   G   S>

240                     255                     270
TCA TTG GCT TCT AAC AGA ATC TTG ACC TTG CCA CAG AGG ACT ATT
 S   L   A   S   N   R   I   L   T   L   P   Q   R   T   I>

285                     300                     315
AGA GGT AAG AAT AAA CAT TGT TGG TCA ACT TCA AAG TCC ACG AGG
 R   G   K   N   K   H   C   W   S   T   S   K   S   T   R>
```

TABLE 3-continued piggyBac ORF Sequence Range: 1 to 1785 (SEQ ID NO: 1)

```
          330             345             360
CGT AGC CGA GTC TCT GCA CTG AAC ATT GTC AGA TCT CAA AGA GGT
 R   S   R   V   S   A   L   N   I   V   R   S   Q   R   G>

375             390             405
CCG ACG CGT ATG TGC CGC AAT ATA TAT GAC CCA CTT TTA TGC TTC
 P   T   R   M   C   R   N   I   Y   D   P   L   L   C   F>

420             435             450
AAA CTA TTT TTT ACT GAT GAG ATA ATT TCG GAA ATT GTA AAA TGG
 K   L   F   F   T   D   E   I   I   S   E   I   V   K   W>

465             480             495
ACA AAT GCT GAG ATA TCA TTG AAA CGT CGG GAA TCT ATG ACA GGT
 T   N   A   E   I   S   L   K   R   R   E   S   M   T   G>

510             525             540
GCT ACA TTT CGT GAC ACG AAT GAA GAT GAA ATC TAT GCT TTC TTT
 A   T   F   R   D   T   N   E   D   E   I   Y   A   F   F>

555             570             585
GGT ATT CTG GTA ATG ACA GCA GTG AGA AAA GAT AAY CAC ATG TCC
 G   I   L   V   M   T   A   V   R   K   D   N   H   M   S>

600             615             630
ACA GAT GAC CTC TTT GAT CGA TCT TTG TCA ATG GTG TAC GTC TCT
 T   D   D   L   F   D   R   S   L   S   M   V   Y   V   S>

645             660             675
GTA ATG AGT CGT GAT CGT TTT GAT TTT TTG ATA CGA TGT CTT AGA
 V   M   S   R   D   R   F   D   F   L   I   R   C   L   R>

690             705             720
ATG GAT GAC AAA AGT ATA CGG CCC ACA CTT CGA GAA AAC GAT GTA
 M   D   D   K   S   I   R   P   T   L   R   E   N   D   V>

735             750             765
TTT ACT CCT GTT AGA AAA ATA TGG GAT CTC TTT ATC CAT CAG TGC
 F   T   P   V   R   K   I   W   D   L   F   I   H   Q   C>

780             795             810
ATA CAA AAT TAC ACT CCA GGG GCT CAT TTG ACC ATA GAT GAA CAG
 I   Q   N   Y   T   P   G   A   H   L   T   I   D   E   Q>

825             840             855
TTA CTT GGT TTT AGA GGA CGG TGT CCG TTT AGG ATG TAT ATC CCA
 L   L   G   F   R   G   R   C   P   F   R   M   Y   I   P>

870             885             900
AAC AAG CCA AGT AAG TAT GGA ATA AAA ATC CTC ATG ATG TGT GAC
 N   K   P   S   K   Y   G   I   K   I   L   M   M   C   D>

915             930             945
AGT GGT ACG AAG TAT ATG ATA AAT GGA ATG CCT TAT TTG GGA AGA
 S   G   T   K   Y   M   I   N   G   M   P   Y   L   G   R>

960             975             990
GGA ACA CAG ACC AAC GGA GTA CCA CTC GGT GAA TAC TAC GTG AAG
 G   T   Q   T   N   G   V   P   L   G   E   Y   Y   V   K>

1005            1020            1035
GAG TTA TCA AAG CCT GTG CAC GGT AGT TGT CGT AAT ATT ACG TGT
 E   L   S   K   P   V   H   G   S   C   R   N   I   T   C>

1050            1065            1080
GAC AAT TGG TTC ACC TCA ATC CCT TTG GCA AAA AAC TTA CTA CAA
 D   N   W   F   T   S   I   P   L   A   K   N   L   L   Q>
```

TABLE 3-continued piggyBac ORF Sequence Range: 1 to 1785 (SEQ ID NO: 1)

```
              1095               1110               1125
GAA CCG TAT AAG TTA ACC ATT GTG GGA ACC GTG CGA TCA AAC AAA
 E   P   Y   K   L   T   I   V   G   T   V   R   S   N   K>

1140               1155               1170
CGC GAG ATA CCG GAA GTA CTG AAA AAC AGT CGC TCC AGG CCA GTG
 R   E   I   P   E   V   L   K   N   S   R   S   R   P   V>

1185               1200               1215
GGA ACA TCG ATG TTT TGT TTT GAC GGA CCC CTT ACT CTC GTC TCA
 G   T   S   M   F   C   F   D   G   P   L   T   L   V   S>

1230               1245               1260
TAT AAA CCG AAG CCA GCT AAG ATG GTA TAC TTA TTA TCA TCT TGT
 Y   K   P   K   P   A   K   M   V   Y   L   L   S   S   C>

1275               1290               1305
GAT GAG GAT GCT TCT ATC AAC GAA AGT ACC GGT AAA CCG CAA ATG
 D   E   D   A   S   I   N   E   S   T   G   K   P   Q   M>

1320               1335               1350
GTT ATG TAT TAT AAT CAA ACT AAA GGC GGA GTG GAC ACG CTA GAC
 V   M   Y   Y   N   Q   T   K   G   G   V   D   T   L   D>

1365               1380               1395
CAA ATG TGT TCT GTG ATG ACC TGC AGT AGG AAG ACG AAT AGG TGG
 Q   M   C   S   V   M   T   C   S   R   K   T   N   R   W>

1410               1425               1440
CCT ATG GCA TTA TTG TAC GGA ATG ATA AAC ATT GCC TGC ATA AAT
 P   M   A   L   L   Y   G   M   I   N   I   A   C   I   N>

1455               1470               1485
TCT TTT ATT ATA TAC AGC CAT AAT GTC AGT AGC AAG GGA GAA AAG
 S   F   I   I   Y   S   H   N   V   S   S   K   G   E   K>

1500               1515               1530
GTC CAA AGT CGC AAA AAA TTT ATG AGA AAC CTT TAC ATG AGC CTG
 V   Q   S   R   K   K   F   M   R   N   L   Y   M   S   L>

1545               1560               1575
ACG TCA TCG TTT ATG CGT AAG CGT TTA GAA GCT CCT ACT TTG AAG
 T   S   S   F   M   R   K   R   L   E   A   P   T   L   K>

1590               1605               1620
AGA TAT TTG CGC GAT AAT ATC TCT AAT ATT TTG CCA AAT GAA GTG
 R   Y   L   R   D   N   I   S   N   I   L   P   N   E   V>

1635               1650               1665
CCT GGT ACA TCA GAT GAC AGT ACT GAA GAG CCA GTA ATG AAA AAA
 P   G   T   S   D   D   S   T   E   E   P   V   M   K   K>

1680               1695               1710
CGT ACT TAC TGT ACT TAC TGC CCC TCT AAA ATA AGG CGA AAG GCA
 R   T   Y   C   T   Y   C   P   S   K   I   R   R   K   A>

1725               1740               1755
AAT GCA TCG TGC AAA AAA TGC AAA AAA GTT ATT TGT CGA GAG CAT
 N   A   S   C   K   K   C   K   K   V   I   C   R   E   H>

1770               1785
AAT ATT GAT ATG TGC CAA AGT TGT TTC TGA
 N   I   D   M   C   Q   S   C   F   *>
```

Example 10

Drug Selection Cassette of PiggyBac Construct

In pXL-BACIII-hDHFR, the drug selection cassette has been re-engineered to have the hrp3 promoter (FIG. 5). The calmodulin promoter of pXL-BACII-hDHFR will be replaced with the hrp3 promoter to create pXL-BACIII-hDHFR. The calmodulin 5'UTR used has bidirectional promoter activity, which will drive transcription of the genes adjacent to the piggyBac insertion. Such expression of the adjacent gene will create a phenotype for the altered expression of the gene.

Example 11

Asymmetric PiggyBac Constructs

The present example is provided to demonstrate the utility of the invention for providing an asymmetric piggyBac transformation vector that includes an asymmetric arrangement of inverted repeat (ITR) elements. These asymmetric piggyBac constructs have the potential for permanently inactivating *P. falciparum* genes in a manner suitable for creation of an attenuated parasite vaccine.

An asymmetric arrangement of the inverted repeats necessary for piggyBac insertion and excision from genomic DNA flank a drug selection cassette or other transgene. piggyBac transposase does not operate by scanning, but identifies the ITR termini directly, so remobilization is unbiased in terms of the ITR used, and an equal number of mobilizations will occur with ITRs in tandem.

This strategy relies on a second mobilization, leaving an orphan arm of the original transposon, which will disrupt the targeted gene, to inactivate expression or generate a direct protein fusion.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

BIBLIOGRAPHY

The following references are hereby specifically incorporated by reference herein in their entirety.
1. van Dijk, M. R., Waters, A. P. & Janse, C. J. Stable transfection of malaria parasite blood stages. *Science* 268, 1358-62 (1995).
2. Crabb, B. S. & Cowman, A. F. Characterization of promoters and stable transfection by homologous and nonhomologous recombination in *Plasmodium falciparum*. *Proc Nati Acad Sci USA* 93, 7289-94 (1996).
3. Waters, A. P., Thomas, A. W., van Dijk, M. R. & Janse, C. J. Transfection of malaria parasites. *Methods: A Comparison of Methods in Enzymology* 13, 134-47 (1997).
4. Wu, Y., Kirkman, L. A. & Wellems, T. E. Transformation of *Plasmodium falciparum* malaria parasites by homologous integration of plasmids that confer resistance to pyrimethamine. *Proceedings of the National Acadamy of Sciences* 93, 1130-1 134 (1996).
5. Greenwood, B. & Mutabingwa, T. Malaria in 2002. *Nature* 415, 670-2 (2002).
6. Maitland, K., Makanga, M. & Williams, T. N. Falciparum malaria: current therapeutic challenges. *Curr Opin Infect Dis* 17, 405-12 (2004).
7. Winstanley, P., Ward, S., Snow, R. & Breckenridge, A. Therapy of falciparum malaria in sub-saharan Africa: from molecule to policy. *Clin Microbiol Rev* 17, 612-637 (2004).
8. Breman, J. G., Alilio, M. S. & Mills, A. Conquering the intolerable burden of malaria: what's new, what's needed: a summary. *Am J Trop Med Hyg* 71, 1-15 (2004).
9. Hartl, D. L. The origin of malaria: mixed messages from genetic diversity. *Nat Rev Microbiol* 2, 15-22 (2004).
10. O'Donnell, R. A. et al. A genetic screen for improved plasmid segregation reveals a role for Rep2O in the interaction of *Plasmodium falciparum* chromosomes. *Embo J* 21, 1231-9 (2002).
11. Kadekoppala, M. et al. Rapid recombination among transfected plasmids, chimeric episome formation and trans gene expression in *Plasmodium falciparum*. *Mol Biochem Parasitol* 112, 211-8 (2001).
12. Sarkar, A. et al. Molecular evolutionary analysis of the widespread piggyBac transposon family and related "domesticated" sequences. *Mol Genet Genomics* 270, 173-80 (2003).
13. Gueiros-Filho, F. J. & Beverley, S. M. Trans-kingdom transposition of the Drosophila element mariner within the protozoan *Leishmania*. *Science* 276, 1716-9 (1997).
14. Mamoun, C. B., Gluzman, I. Y., Beverley, S. M. & Goldberg, D. E. Transposition of the Drosophila element mariner within the human malaria parasite *Plasmodium falciparum*. *Mol Biochem Parasitol* 110, 405-7 (2000).
15. Fraser, M. J., Smith, G. E. & Summers, M. D. Acquisition of Host Cell DNA Sequences by Baculoviruses: Relationship Between Host DNA Insertions and FP Mutants of *Autographa californica* and *Galleria mellonella* Nuclear Polyhedrosis Viruses. *Journal of Virology* 47, 287-300 (1983).
16. Fraser, M. J., Brusca, J. S., Smith, G. E. & Summers, M. D. Transposon-mediated mutagenesis of a baculovirus. *Virology* 145, 356-61 (1985).
17. Cary, L. C. et al. Transposon mutagenesis of baculoviruses: analysis of *Trichoplusia ni* transposon IFP2 insertions within the FP-locus of nuclear polyhedrosis viruses. *Virology* 172, 156-69 (1989).
18. Wang, H. H., Fraser, M. J. & Cary, L. C. Transposon mutagenesis of baculoviruses: analysis of TFP3 lepidopteran transposon insertions at the FP locus of nuclear polyhedrosis viruses. *Gene* 81, 97-108 (1989).
19. Thibault, S. T. et al. A complementary transposon tool kit for Drosophila melanogaster using P and piggyBac. *Nat Genet* 36, 283-7 (2004).
20. Ryder, E. & Russell, S. Transposable elements as tools for genomics and genetics in Drosophila. *Brief Funct Genomic Proteomic* 2, 57-71 (2003).
21. Lobo, N. F., Hua-Van, A., Li, X., Nolen, B. M. & Fraser, M. J., Jr. Germ line transformation of the yellow fever mosquito, *Aedes aegypti*, mediated by transpositional insertion of a piggyBac vector. *Insect Mol Biol* 11, 133-9 (2002).
22. Toshiki, T. et al. Germline transformation of the silkworm *Bombyx mori* L. using a piggyBac transposon-derived vector. *Nat Biotechnol* 18, 81-4 (2000).
23. Grossman, G. L, Rafferty, C. S., Fraser, M. J. & Benedict, M. Q. The piggyBac element is capable of precise excision and transposition in cells and embryos of the mosquito, *Anopheles gambiae*. *Insect Biochem Mol Biol* 30, 909-14 (2000).
24. Li, X. et al. piggyBac internal sequences are necessary for efficient transformation of target genomes. *Insect Mol Biol* 14, 17-30 (2005).
25. Trang, D. T., Huy, N. T., Kariu, T., Tajima, K. & Kamei, K. One-step concentration of malarial parasite-infected red blood cells and removal of contaminating white blood cells. *Malar J* 3, 1-7 (2004).
26. Deitsch, K., Driskill, C. & Wellems, T. Transformation of malaria parasites by the spontaneous uptake and expression of DNA from human erythrocytes. *Nucleic Acids Res.* 29, 850-3 (2001).
27. Schlichtherle, M., Wahigren, M., Perlmann, H. & Scherf, A. Methods in Malaria Research (MR4/ATCC, 2000).
28. Earp, D. J., Lowe, B. & Baker, B. Amplification of genomic sequences flanking transposable elements in host and heterologous plants: a tool for transposon tagging and genome characterization. *Nucleic Acids Res* 18, 327-1-9 (1990).
29. Gardner, M. J. et al. Genome sequence of the human malaria parasite *Plasmodium falciparum*. *Nature* 419, 498-511 (2002).
30. Watanabe, J., Sasaki, M., Suzuki, Y. & Sugano, S. FULL-malaria: a database for a full-length enriched cDNA library from human malaria parasite, *Plasmodium falciparum*. *Nucleic Acids Res* 29, 70-1 (2001).

What is claimed is:

1. A method for genetically modifying a *Plasmodium* parasite by insertional mutagenesis comprising: (a) preparing a minimum piggyBac transposon vector comprising a minimal piggyBac transposon containing a human dihydrofolate reductase (hdhfr) coding sequence under the control of a *Plasmodium* 5' calmodulin regulatory element and a 3' histidine rich protein-2 regulatory element; (b) preparing a helper plasmid comprising a piggyBac transposase coding sequence; (c) isolating a preparation of blood-stage *Plasmodium* parasites; and (d) introducing said minimum piggyBac transposon vector and said helper plasmid to said preparation of blood-stage *Plasmodium* parasites to provide a transformed *Plasmodium* parasite, wherein said piggyBac transposase coding sequence encodes a protein sequence provided by SEQ ID NO: 2.

2. The method of claim 1, wherein said *Plasmodium* parasite is *Plasmodium falciparum*.

3. The method of claim 1, wherein the insertional mutagenesis occurs in 3 or more locus sites of said transformed *Plasmodium* parasite.

4. The method of claim 1, wherein the insertional mutagenesis has an efficiency of about $7.5 \times 10^{-6}$ to about $1.1 \times 10^{-3}$.

5. The method of claim 1, wherein the *Plasmodium* parasite is stable for 20 generations of passage or more in the absence of a helper plasmid.

6. The method of claim 1, wherein said introducing step (d) comprises:
   (i) loading said minimum piggyBac transposon vector and said helper plasmid into a population of erythrocytes via electroporation; and
   (ii) combining said population of erythrocytes loaded with said minimum piggyBac transposon vector and said helper plasmid with said preparation of blood-stage *Plasmodium* parasites.

7. The method of claim 1 wherein said isolating step (c) comprises: preparing said preparation of blood-stage Plasmodium parasites via passage through a magnetic column.

8. A method for genetically modifying a Plasmodium parasite by insertional mutagenesis comprising: (a) preparing a minimal piggyBac transposon vector comprising a minimal piggyBac transposon containing a selectable marker under the control of a *Plasmodium* 5' calmodulin regulatory element and a 3' histidine rich protein-2 regulatory element; (b) preparing a helper plasmid comprising a piggyBac transposase coding sequence; (c) isolating a preparation of blood-stage *Plasmodium* parasites; and (d) introducing said minimal piggyBac transposon and said helper plasmid to said preparation of blood-stage *Plasmodium* parasites to provide a transformed *Plasmodium* parasite, wherein said piggyBac transposase coding sequence encodes a protein sequence provided by SEQ ID NO: 2.

9. The method of claim 8, wherein the insertional mutagenesis has an efficiency of about $7.5 \times 10^{-6}$ to about $1.1 \times 10^{-3}$.

10. A method for genetically modifying a *Plasmodium* parasite by insertional mutagenesis comprising: (a) preparing a minimal piggyBac transposon vector comprising a minimal piggyBac transposon containing a selectable marker under the control of a *Plasmodium* 5' regulatory element and a *Plasmodium* 3' regulatory element; (b) preparing a helper plasmid comprising a piggyBac transposase coding sequence; (c) isolating a preparation of blood-stage *Plasmodium* parasites; and (d) introducing said minimal piggyBac transposon and said helper plasmid to said preparation of blood-stage *Plasmodium* parasites to provide a transformed *Plasmodium* parasite, wherein said piggyBac transposase coding sequence encodes a protein sequence provided by SEQ ID No: 2.

11. The method of claim 10, wherein said *Plasmodium* 5' regulatory element is derived from a *Plasmodium* calmodulin gene, a *Plasmodium* heat shock protein 86 (hsp86) gene, a *Plasmodium* histidine-rich protein 2 (hrp2) gene, a *Plasmodium* histidine-rich protein 3 (hrp3) gene, or a *Plasmodium* dihydrofolate reductase-thymidylate synthase (dhfr-ts) gene.

12. The method of claim 10, wherein said *Plasmodium* 5' regulatory element comprises a 5' *Plasmodium* calmodulin regulatory element and a 5' *Plasmodium* dihydrofolate reductase-thymidylate synthase (dhfr-ts) regulatory element in a head-to-head arrangement.

13. The method of claim 10, wherein said *Plasmodium* 3' regulatory element is derived from a *Plasmodium* calmodulin gene, a *Plasmodium* heat shock protein 86 (hsp86) gene, a *Plasmodium* histidine-rich protein 2 (hrp2) gene, a *Plasmodium* histidine-rich protein 3 (hrp3) gene, or a *Plasmodium* dihydrofolate reductase-thymidylate synthase (dhfr-ts) gene.

14. The method of claim 10, wherein said introducing step (b) comprises: (i) loading said minimal piggyBac transposon vector and said helper plasmid into a population of erythrocytes via electroporation; and (ii) combining said population of erythrocytes loaded with said piggyBac transposon vector and said helper plasmid with said preparation of blood-stage parasites.

15. The method of claim 10, wherein said isolating step (a) comprises: preparing said preparation of blood-stage *Plasmodium* parasites via passage through a magnetic column.

16. The method of claim 10, wherein said selectable marker comprises the human dihydrofolate reductase (hdhfr) coding sequence.

17. The method of claim 10, wherein the insertional mutagenesis has an efficiency of about $7.5 \times 10^{-6}$ to about $1.1 \times 10^{-3}$.

18. A method of genetically modifying a *Plasmodium* parasite by insertional mutagenesis comprising: (a) isolating a preparation of blood-stage *Plasmodium* parasites; and (b) introducing a minimal piggyBac transposon vector and a helper plasmid to said preparation of blood-stage *Plasmodium* parasites to provide a transformed *Plasmodium* parasite, wherein said minimal piggyBac transposon vector comprises a minimal piggyBac transposon containing a selectable marker under the control of a *Plasmodium* 5' calmodulin regulatory element and a 3' *Plasmodium* histidine rich protein-2 regulatory element, and wherein said helper plasmid comprises a piggyBac transposase coding sequence, wherein said piggyBac transposase coding sequence encodes a protein sequence provided by SEQ ID No: 2.

19. The method of claim 18, wherein said piggyBac transposase coding sequence of said helper plasmid is under the control of a *Plasmodium* 5' regulatory element and a 3' *Plasmodium* regulatory element.

20. The method of claim 18, wherein said selectable marker comprises the human dihydrofolate reductase (hdhfr) coding sequence.

21. The method of claim 18, wherein the insertional mutagenesis has an efficiency of about $7.5 \times 10^{-6}$ to about $1.1 \times 10^{-3}$.

22. A method for genetically modifying a *Plasmodium* parasite comprising:
(a) isolating a preparation of blood-stage *Plasmodium* parasites; and
(b) introducing a minimal piggyBac transposon vector and a helper plasmid to said preparation of blood-stage *Plasmodium* parasites to provide a transformed *Plasmodium* parasite,
wherein said minimal piggyBac transposon vector comprises a minimal piggyBac transposon containing a selectable marker under the control of a *Plasmodium* 5' regulatory element and a 3' *Plasmodium* regulatory element, and wherein said helper plasmid comprises a piggyBac transposase coding sequence,
wherein said piggyBac transposase coding sequence encodes a protein sequence provided by SEQ ID No: 2.

23. The method of claim 22, wherein said *Plasmodium* 5' regulatory element is derived from a *Plasmodium* calmodulin gene, a *Plasmodium* heat shock protein 86 (hsp86) gene, a *Plasmodium* histidine-rich protein 2 (hrp2) gene, a *Plasmodium* histidine-rich protein 3 (hrp3) gene, or a *Plasmodium* dihydrofolate reductase-thymidylate synthase (dhfr-ts) gene.

24. The method of claim 22, wherein said *Plasmodium* 5' regulatory element comprises a 5' *Plasmodium* calmodulin regulatory element and a 5' *Plasmodium* dihydrofolate reductase-thymidylate synthase (dhfr-ts) regulatory element in a head-to-head arrangement.

25. The method of claim 22, wherein said *Plasmodium* 3' regulatory element is derived from a *Plasmodium* calmodulin gene, a *Plasmodium* heat shock protein 86 (hsp86) gene, a *Plasmodium* histidine-rich protein 2 (hrp2) gene, a *Plasmodium* histidine-rich protein 3 (hrp3) gene, or a *Plasmodium* dihydrofolate reductase-thymidylate synthase (dhfr-ts) gene.

26. A method for genetically modifying a *Plasmodium* parasite comprising:
(a) isolating a preparation of blood-stage *Plasmodium* parasites; and
(b) introducing a piggyBac transposon vector and a helper plasmid to said preparation of blood-stage *Plasmodium* parasites to provide a transformed *Plasmodium* parasite,
wherein said piggyBac transposon vector comprises a piggyBac transposon containing a selectable marker under the control of a *Plasmodium* 5' regulatory element and a 3' *Plasmodium* regulatory element, and wherein said helper plasmid comprises a piggyBac transposase coding sequence,
wherein said piggyBac transposase coding sequence encodes a protein sequence provided by SEQ ID NO:2.

27. The method of claim 26, wherein said *Plasmodium* 5' regulatory element is derived from a *Plasmodium* calmodulin gene, a *Plasmodium* heat shock protein 86 (hsp86) gene, a *Plasmodium* histidine-rich protein 2 (hrp2) gene, a *Plasmodium* histidine-rich protein 3 (hrp3) gene, or a *Plasmodium* dihydrofolate reductase-thymidylate synthase (dhfr-ts) gene.

28. The method of claim 26, wherein said *Plasmodium* 5' regulatory element comprises a 5' *Plasmodium* calmodulin regulatory element and a 5' *Plasmodium* dihydrofolate reductase-thymidylate synthase (dhfr-ts) regulatory element in a head-to-head arrangement.

29. The method of claim 26, wherein said *Plasmodium* 3' regulatory element is derived from a *Plasmodium* calmodulin gene, a *Plasmodium* heart shock protein 86 (hsp86) gene, a *Plasmodium* histidine-rich protein 2 (hrp2) gene, a *Plasmodium* histidine-rich protein 3 (hrp3) gene, or a *Plasmodium* dihydrofolate reductase-thymidylate synthase (dhfr-ts) gene.

* * * * *